United States Patent [19]
Eicken et al.

[11] Patent Number: 4,593,104
[45] Date of Patent: Jun. 3, 1986

[54] 2-HALO-N-(AZOLE-1-YL-METHYL)-SUBSTITUTED ACETANILIDES

[75] Inventors: Karl Eicken, Wachenheim; Wolfgang Rohr, Mannheim; Bernd Zeeh, Ludwigshafen; Bruno Würzer, Limburgerhof, all of Fed. Rep. of Germany

[73] Assignee: BASF Aktiengesellschaft, Fed. Rep. of Germany

[21] Appl. No.: 839,777

[22] Filed: Oct. 6, 1977

[30] Foreign Application Priority Data

Oct. 23, 1976 [DE] Fed. Rep. of Germany ....... 2648008

[51] Int. Cl.$^4$ .................. C07D 231/12; C07D 233/61
[52] U.S. Cl. ........................................ 548/262; 71/92; 71/93; 71/95; 548/251; 548/253; 548/255; 548/264; 548/265; 548/269; 548/337; 548/341; 548/342; 548/343; 548/376; 548/377; 548/378; 548/561

[58] Field of Search ............... 548/375, 376, 377, 378, 548/341, 337, 253, 255, 264, 262, 269, 265, 561; 71/92, 95; 260/308 R, 308 A, 308 D, 326.43

[56] References Cited

U.S. PATENT DOCUMENTS

| 3,547,620 | 12/1970 | Olin | 71/118 |
| 3,769,301 | 10/1973 | Olin | 71/118 |
| 3,907,544 | 9/1975 | Olin | 71/92 |
| 4,055,410 | 10/1977 | Cheng | 71/92 |
| 4,517,011 | 5/1985 | Thomas et al. | 71/92 |

FOREIGN PATENT DOCUMENTS 1014380 8/1957 Fed. Rep. of Germany .
2405510 5/1973 Fed. Rep. of Germany :

Primary Examiner—Richard L. Raymond
Attorney, Agent, or Firm—Keil & Weinkauf

[57] ABSTRACT

New and valuable 2-halo-N-(azole-1-yl-methyl)-substituted acetanilides and having a good herbicidal action, and methods of controlling the growth of unwanted plants with these compounds.

12 Claims, No Drawings

2-HALO-N-(AZOLE-1-YL-METHYL)-SUBSTITUTED ACETANILIDES

The present invention relates to new and valuable acetanilides, methods of manufacturing them, herbicides containing these compounds, and methods of controlling the growth of unwanted plants with these compounds.

Haloacetanilides having herbicidal or growth-regulating properties are known from the literature. Of particular importance are active ingredients such as 2-chloro-N-isopropylacetanilide (German No. 1,014,380) and 2-chloro-2',6'-diethyl-N-methoxymethyl-acetanilide (U.S. Pat. No. 3,547,620). Furthermore, haloacetanilides with heterocyclic substituents have been disclosed, e.g., compounds bearing a 1,3-dioxolan-2-ylmethyl group on the nitrogen atom (German Laid-Open Application DOS No. 2,405,510). In the examples in these publications illustrating activity, it is apparent that the action of the compounds mentioned therein is restricted to a few grassy species generally easily combatted with haloacetanilides. Moreover, the relatively high dosage rates employed for some of these prior art compounds are indicative of low activity.

We have found that acetanilides of the formula

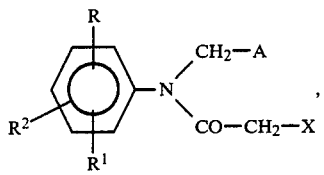

where R denotes hydrogen, alkyl of a maximum of 5 carbon atoms, or alkoxy of a maximum of 5 carbon atoms, $R^1$ denotes hydrogen, halogen, alkyl of a maximum of 5 carbon atoms, alkoxy of a maximum of 5 carbon atoms, perhaloalkyl of a maximum of 4 carbon atoms, or 1-alkoxyalkyl of a maximum of 5 carbon atoms, $R^2$ denotes hydrogen, halogen, alkyl of a maximum of 5 carbon atoms, alkoxy of a maximum of 5 carbon atoms, perhaloalkyl of a maximum of 4 carbon atoms, or alkoxyalkyl of a maximum of 5 carbon atoms, or forms, together with R, an alkylene chain of a maximum of 6 carbon atoms which is attached in the orthoposition and is optionally substituted by alkyl of a maximum of 4 carbon atoms, X denotes chloro, bromo, or iodo, and A denotes azole which is linked via a ring nitrogen atom and is unsubstituted or mono- or polysubstituted by halogen, phenyl, alkyl, alkoxy, alkylthio or perfluoroalkyl, each of a maximum of 4 carbon atoms, cyano, carboxy, carbalkoxy of a maximum of 4 carbon atoms in the alkoxy group, or alkanoyl of a maximum of 4 carbon atoms, A also being able to denote salts of azoles containing 2 or 3 nitrogen atoms, have a surprisingly strong and selective herbicidal action.

In view of the state of the art, it was surprising that the heterocyclic substituted acetanilides according to the invention exhibit such an excellent and intense action on a broad spectrum of unwanted plants. Depending on the objective, the new active ingredients are suitable for the total removal of plant growth, for the selective elimination of unwanted plants from specific herbaceous or woody crop plants, or for growth regulation by inhibition.

Particularly marked selectivity between weeds and crop plants is exhibited even at low application rates by compounds of the invention according to the formula I in which R and $R^1$ are substituents in the 2- and 6-positions on the phenyl nucleus and each denotes alkyl of a maximum of 5 carbon atoms.

Suitable meanings for R, $R^1$, $R^2$, X and A in formula I are as follows:

R: hydrogen, alkyl of a maximum of 5 carbon atoms, such as methyl, ethyl, n-propyl, isopropyl, n-butyl, sec-butyl, isobutyl, tert-butyl, linear and branched pentyl, alkoxy of a maximum of 5 carbon atoms such as methoxy, ethoxy, propoxy, butoxy and pentyloxy;

$R^1$: hydrogen, halogen, alkyl of a maximum of 5 carbon atoms, such as methyl, ethyl, n-propyl, isopropyl, n-butyl, sec-butyl, isobutyl, tert-butyl, linear and branched pentyl, alkoxy of a maximum of 5 carbon atoms, such as methoxy, ethoxy, propoxy, butoxy, pentyloxy, perhaloalkyl of a maximum of 4 carbon atoms, such as trifluoromethyl, trichloromethyl, pentafluoroethyl, heptafluoroisopropyl, alkoxyalkyl of a maximum of 5 carbon atoms, such as methoxymethyl and ethoxyethyl;

$R^2$: hydrogen, halogen, alkyl of a maximum of 5 carbon atoms, such as methyl, ethyl, n-propyl, isopropyl, n-butyl, sec-butyl, isobutyl, tert-butyl, linear and branched pentyl, alkoxy of a maximum of 5 carbon atoms, such as methoxy, ethoxy, propoxy, butoxy, pentyloxy, perhaloalkyl of a maximum of 4 carbon atoms, such as trifluoromethyl, trichloromethyl, pentafluoroethyl, heptafluoroisopropyl, alkoxyalkyl of a maximum of 5 carbon atoms, such as methoxymethyl and ethoxymethyl;

$R^2$ together with R: an alkylene chain of a maximum of 6 carbon atoms which is attached in the ortho-position and is optionally substituted by alkyl of a maximum of 4 carbon atoms, such as ethylene, trimethylene, tetramethylene, 1-methyltrimethylene, 1,1-dimethyltrimethylene, 1,1-dimethyltetramethylene;

X: chlorine, bromine, and iodine, preferably chlorine;

A: azole linked by a ring nitrogen atom, such as pyrrole, pyrazole, 1,2,4-triazole, 1,2,3-triazole, or tetrazole, which is unsubstituted or mono- or polysubstituted by halogen, phenyl, alkyl, alkoxy, alkylthio or perfluoroalkyl, each of a maximum of 4 carbon atoms, cyano, carboxy, carbalkoxy with a maximum of 4 carbon atoms in the alkoxy group, or alkanoyl of a maximum of 4 carbon atoms, the substituents being identical or different, e.g., 2,6-dimethylpyrrole, tetramethylpyrrole, 3(5)-methylpyrazole, 4-methylpyrazole, 3(5)-ethylpyrazole, 4-ethylpyrazole, 3(5)-isopropylpyrazole, 4-isopropylpyrazole, 3,5-dimethylpyrazole, 3,5-dimethyl-4-acetylpyrazole, 3,5-dimethyl-4-propionylpyrazole, 3,4,5-trimethylpyrazole, 3(5)-phenylpyrazole, 4-phenylpyrazole, 3,5-diphenylpyrazole, 3(5)-phenyl-5(3)-methylpyrazole, 3(5)-chloropyrazole, 4-chloropyrazole, 4-bromopyrazole, 4-iodopyrazole, 3,4,5-trichloropyrazole, 3,4,5-tribromopyrazole, 3,5-dimethyl-4-chloropyrazole, 3,5-dimethyl-4-bromopyrazole, 4-chloro-3(5)-methylpyrazole, 4-bromo-3(5)-methylpyrazole, 4-methyl-3,5-dichloropyrazole, 3(5)-methyl-4,5(3)-dichloropyrazole, 3(5)-chloro-5(3)-methylpyrazole, 4-methoxypyrazole, 3(5)-methyl-5(3)-methoxypyrazole, 3(5)-ethoxy-4,5(3)-dimethylpyrazole, 3(5)-methyl-5(3)-trifluoromethylpyrazole, 3,5-bis-trifluoromethylpyrazole, 3(5)-methyl-5(3)-carbethoxypyrazole, 3,5-bis-carboethoxypyrazole, 3,4,5-triscarbethoxypyrazole, 3(5)-methyl-5(3)-methylthio-4-carbethoxypyrazole, 4-methyl-3,5-bis-carbethoxypyrazole, 4-cyanopyrazole, 4-methoxy-3,5-dichloropyrazole, 3(5)-methyl-1,2,4-triazole, 3,5-dimethyl-1,2,4-triazole, 3(5)-chloro-1,2,4-triazole, 3(5)-bromo-1,2,4-triazole, 3(5)-chloro-5(3)-methyl-1,2,4-triazole, 3,5-dichloro-1,2,4-triazole, 3,5-dibromo-1,2,4-triazole, 3(5)-chloro-5(3)-cyano-1,2,4-triazole, 3(5)-chloro-5(3)-phenyl-1,2,4-triazole, 3(5)-chloro-5(3)-carbomethoxy-1,2,4-triazole, 3(5)-methylthio-1,2,4-triazole, 4(5)-methyl-1,2,3-triazole, 4,5-dimethyl-1,2,3-triazole, 4(5)-phenyl-1,2,3-triazole, 4(5)-chloro-1,2,3-triazole, 1,2,3-triazol-4(5)-yl carboxylic acid ethyl ester, 1,2,3-triazol-4,5-yl dicarboxylic acid dimethyl ester, 5-methyltetrazole, 5-chlorotetrazole, tetrazolyl-5-carboxylic acid ethyl ester, imidazole, 2-methylimidazole, 4,5-dichloroimidazole, 2-methyl-4,5-dichloroimidazole, 2-ethyl-4,5-dichloroimidazole, 2-isopropyl-4,5-dichloroimidazole, 2,4,5-trichloroimidazole, 2,4,5-tribromoimidazole, and 2-bromo-4,5-dichloroimidazole.

Furthermore, the radical A, when the optionally substituted azole contains 2 or 3 nitrogen atoms, may be bound to one of the usual strong inorganic or organic acids, e.g., hydrochloric acid, hydrobromic acid, nitric acid, sulfuric acid, tetrafluoboric acid, fluosulfonic acid, and formic acid, a halogenated carboxylic acid, e.g., trichloroacetic acid, an alkanesulfonic acid, e.g., methanesulfonic acid, a halogenated alkanesulfonic acid, e.g., trifluoromethanesulfonic acid and perfluorohexanesulfonic acid, or an arylsulfonic acid, e.g., dodecylbenzenesulfonic acid, to give a salt.

With certain asymmetrically substituted azoles, e.g., pyrazole, 1,2,3-triazole and 1,2,4-triazole, two isomers appear because of tautomeric structures in the starting materials; pyrazole is given here by way of example:

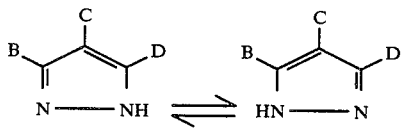

In these instances, two isomers appear in the compounds of the formula I; their ratio to each other is essentially determined by the kind of radicals B, C and D, and may be of importance for the herbicidal properties.

The new acetanilides of the formula I may be prepared by the following processes.

The acetanilides of the formula I are obtained by reaction of 2-halo-N-halomethyl acetanilides of the formula II with a 1H azole of the formula H-A in accordance with the equation

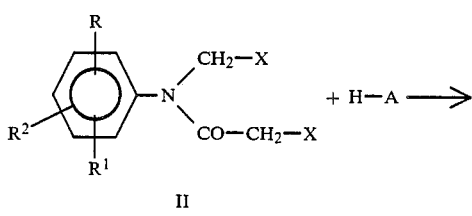

II

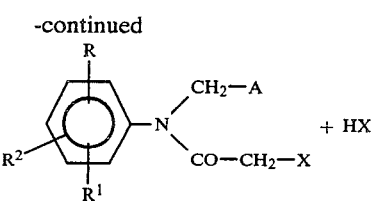

I

The substituents R, $R^1$, $R^2$ and X have the above meanings and A denotes azole attached via a ring nitrogen atom and which is unsubstituted or mono- or polysubstituted by halogen, phenyl, alkyl, alkoxy, alkylthio or perfluoroalkyl, each of a maximum of 4 carbon atoms, cyano, carboxy, carbalkoxy with a maximum of 4 carbon atoms in the alkoxy group, or alkanoyl with a maximum of 4 carbon atoms.

Some of the 2-halo-N-halomethyl acetanilides of the formula II are known from German Published Application DAS No. 1,542,950; others may be prepared analogously by reaction of the appropriate azomethines with a haloacetyl halide.

The 1H azole is expediently employed in at least a molar amount, with reference to 2-halo-N-halomethyl acetanilide.

The hydrogen halide liberated during the reaction is advantageously intercepted by suitable binding agents such as organic bases, e.g., tertiary amines, or organic bases, e.g., alkali metal or alkaline earth metal carbonates or bicarbonates. The hydrogen halide binder is added in an at least molar amount, with reference to 1H azole employed.

It is advantageous to carry out the reaction in a solvent inert to 2-halo-N-halomethyl acetanilides. Suitable solvents are hydrocarbons, e.g., petroleum ether, ligroin, cyclohexane, toluene and xylene; ethers, e.g., diethyl ether, diisopropyl ether, dimethoxyethane, tetrahydrofuran, dioxane, and anisole; halogenated hydrocarbons, e.g., dichloromethane, chloroform, 1,2-dichloroethane, carbon tetrachloride, and chlorobenzene; ketones, e.g., acetone, and methyl ethyl ketone; esters, e.g., ethyl acetate, and butyl acetate; and sulfones, e.g., dimethyl sulfoxide, and tetrahydrothiophene-1,1-dioxide. Mixtures of these solvents may also be used.

The reaction may be carried out at temperatures of from 0° C. upwards. To accelerate the reaction, it is advantageous to carry it out at the boiling point of the solvent or solvent mixture, but not above 200° C. Preferred temperatures are from 50° to 150° C. Upon completion of the reaction the mixture is subjected to filtration and the product is, if desired after washing, isolated from the filtrate in conventional manner. If a solvent miscible with water is used, it is usually advantageous to remove it, after filtration, by evaporation and to replace it by a solvent immiscible with water.

The new acetanilides of the formula I may also be prepared by reaction of 2-halo-N-halomethyl acetanilides of the formula II with a salt of an azole of the formula $M^\oplus A^\ominus$, in accordance with the following equation:

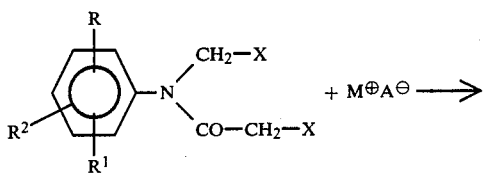

II

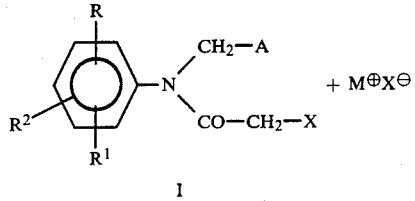 + M⊕A⊖ ⟶

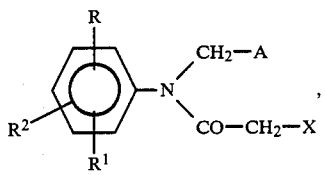 + M⊕X⊖

I

The substituents R, $R^1$, $R^2$ and X have the above meanings, M⊕ denotes a silver ion, an alkali metal ion or an equivalent of an alkaline earth metal ion, and A denotes azole attached via a ring nitrogen atom and which is unsubstituted or mono- or polysubstituted by halogen, phenyl, alkyl, alkoxy, alkylthio or perfluoroalkyl, each of a maximum of 4 carbon atoms, cyano, carboxy, carbalkoxy of a maximum of 4 carbon atoms in the alkoxy group, or alkanoyl of a maximum of 4 carbon atoms.

The alkali metal, alkaline earth metal or silver azoles M⊕A⊖ are prepared in known manner by reaction of the 1H azole H-A with alkali metals or strong bases, e.g., alkali metal hydroxide, alkali metal alcoholate, alkali metal amide, alkali metal hydride, and silver hydroxide, with the liberation of hydrogen, alcohol or ammonia.

The reaction of the salts of M⊕A⊖ with the 2-halo-N-halomethyl acetanilides of the formula II is advantageously carried out in polar aprotic solvents such as nitriles, e.g., acetonitrile, amides, e.g., dimethylformamide, polyethers, e.g., diethylene glycol dimethyl ether and triethylene glycol dimethyl ether, sulfones, e.g., tetrahydrothiophene-1,1-dioxide, sulfoxides, e.g., dimethyl sulfoxide, and ketones, e.g., acetone, methyl ethyl ketone and diisopropyl ketone, at temperatures of from −30° to +50° C., preferably at room temperature. The starting materials are expediently employed in equimolar amounts. The reaction products are—if desired, after separation of the inorganic salts M⊕A⊖ formed and if desired after replacement of the polar aprotic solvent by a solvent immiscible with water—isolated in conventional manner.

Acetanilides of the formula I

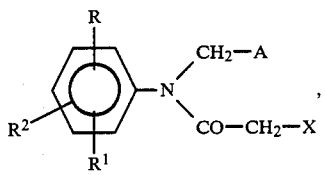

where R, $R^1$, $R^2$ and X have the above meanings and A denotes azole (with 2 or 3 nitrogen atoms in the ring) attached via a ring nitrogen atom and unsubstituted or mono- or polysubstituted by halogen, phenyl, alkyl, alkoxy, alkylthio or perfluoroalkyl, each of a maximum of 4 carbon atoms, cyano, carboxy, carbalkoxy of a maximum of 4 carbon atoms in the alkoxy group, or alkanoyl of a maximum of 4 carbon atoms, may be prepared by reaction of substituted anilines of the formula III with a hydrohalide, preferably hydrochloride, of a halomethyl azole of the formula X—CH₂—A to give a secondary aniline of the formula IV, and by further reaction of this secondary aniline with a haloacetyl halide of the formula X—CO—CH₂—X in accordance with the equation

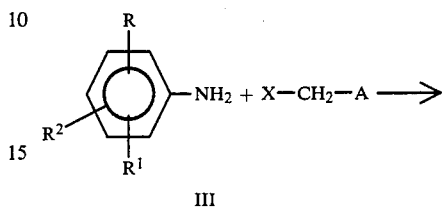

III

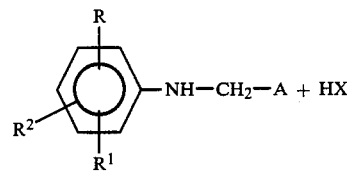

IV

IV + X—CO—CH₂—X ⟶ I + HX

As halomethyl azoles, chloromethyl azoles are preferred. Chloromethylpyrazole hydrochloride and its manufacture are disclosed in J. Chem. Soc., 1960, 5272-3. Other chloromethyl azoles may be prepared analogously.

With asymmetrically substituted chloromethyl azoles in which the azole is a pyrazole, a 1,2,3-triazole or a 1,2,4-triazole, two isomers also appear because of tautomeric structures.

Both process steps require the presence of an agent which binds hydrogen halide; suitable compounds for the first stage are tertiary organic amines such as triethylamine, ethyl diisopropylamine, diazabicyclo-[2,2,2]-octane, diethylcyclohexylamine, pyridine, and alkylpyridine, and organic bases such as alkali metal or alkaline earth metal carbonates or bicarbonates, or substituted anilines of the formula III; suitable compounds for the second stage are only the first mentioned bases and not the substituted anilines.

Both reactions are advantageously carried out in a polar aprotic solvent such as nitriles, e.g., acetonitrile, amides, e.g., dimethylformamide, polyethers, e.g., diethylene glycol dimethyl ether, and triethylene glycol dimethyl ether, sulfones, e.g., tetrahydrothiophene-1,1-dioxide, sulfoxides, e.g., dimethyl sulfoxide, and ketones, e.g. acetone, methyl ethyl ketone, and diisopropyl ketone.

The reaction to give the secondary aniline of the formula IV takes place in the temperature range of from 20° to 150° C.; the further reaction with the haloacetyl halide in the range of from −20° to +100° C.

The starting materials are advantageously employed in equimolar amounts. The secondary aniline of the formula IV may, if desired, be further reacted with haloacetyl halides without being isolated.

Acetanilides of the formula I

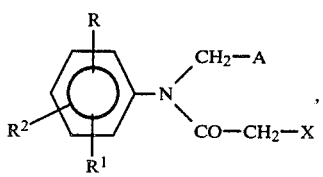

where R, $R^1$, $R^2$ and X have the above meanings and A denotes a 1,2,3-triazole attached via a ring nitrogen atom and unsubstituted or mono- or polysubstituted by phenyl, alkyl of a maximum of 4 carbon atoms, carboxy, or carbalkoxy with a maximum of 4 carbon atoms in the alkoxy group, may also be obtained by reaction of 2-halo-N-halomethyl acetanilides of the formula II with an alkali metal azide and further reaction of the 2-halo-N-azidomethyl acetanilide of the formula V, thus obtained, with acetylene, the hydrogen atoms of which may be replaced by the groups given as substituents for the triazolyl radical, in accordance with the following equation:

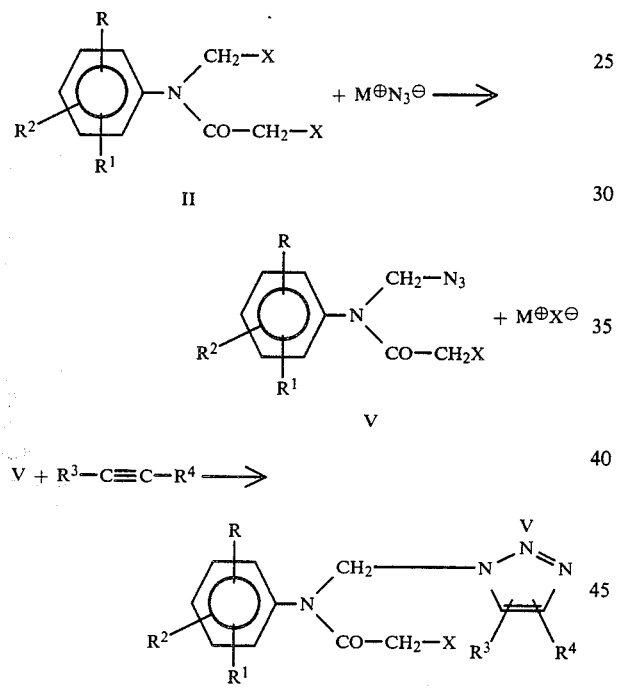

R, $R^1$, $R^2$ and X have the above meanings, $M^\oplus$ denotes an alkali metal ion, $R^3$ and $R^4$ are identical or different and each denotes hydrogen, phenyl, alkyl of a maximum of 4 carbon atoms, carboxy, carbalkoxy of a maximum of 4 carbon atoms in the alkoxy group, or alkanoyl of a maximum of 4 carbon atoms.

The 2-halo-N-halomethyl acetanilides of the formula II are reacted with at least molar amounts of an alkali metal azide, preferably sodium azide, in an aprotic polar solvent at temperatures of from $-30°$ to $+50°$ C., preferably room temperature.

Particularly suitable aprotic polar solvents are tertiary amides such as dimethylformamide and N,N-dimethylacetamide, nitriles such as acetonitrile, and sulfones such as tetrahydrothiophene-1,1-dioxide and dimethyl sulfoxide.

The 2-halo-N-azidomethyl acetanilide of the formula V is expediently reacted as crude product with at least molar amounts of acetylene or an acetylene derivative in a solvent inert to the reactants to give a 2-halo-N-(1,2,3-triazol-1-yl-methyl)-acetanilide. It is advantageous to remove, before the reaction, the alkali metal azide still present by washing with water.

The reaction with acetylene or an acetylene derivative may, depending on the reactivity of the reactants, be carried out at from 0° to 150° C. and at atmospheric or superatmospheric pressure. Suitable solvents inert to the reactants are aprotic nonpolar solvents such as chlorinated aliphatic and aromatic hydrocarbons, e.g., dichloromethane, carbon tetrachloride, 1,2-dichloroethane and chlorobenzenes, and ethers such as diethyl ether, dioxane, tetrahydrofuran and anisole.

The salts of the acetanilides of the formula I, A denoting an azole with 2 or 3 nitrogen atoms, preferably pyrazole, 1,2,3-triazole and 1,2,4-triazole, may be obtained in conventional manner from the acetanilides of the formula I, which may be prepared by one of the processes described above, by adding at least a molar amount of a strong inorganic or organic acid, e.g., hydrochloric acid, hydrobromic acid, nitric acid, sulfuric acid, tetrafluoboric acid, fluosulfonic acid and formic acid, a halogenated carboxylic acid, e.g., trichloroacetic acid, an alkanesulfonic acid, e.g., methanesulfonic acid, a halogenated alkanesulfonic acid, e.g., trifluoromethanesulfonic acid and perfluorohexanesulfonic acid, or an arylsulfonic acid, e.g., dodecylbenzenesulfonic acid.

The preparation of the new acetanilides and salts thereof is illustrated by the following examples, in which parts by weight bear the same relationship to parts by volume as kilograms to liters.

EXAMPLE 1

16.5 parts by weight of 2-chloro-2',6'-dimethyl-N-chloromethyl acetanilide and 9.3 parts by weight of 1,2,4-triazole are refluxed for 8 hours in 60 parts by volume of anhydrous tetrahydrofuran. After the mixture has been cooled, it is filtered, the filtrate is concentrated in vacuo, and the residue is dissolved in 60 parts by volume of chloroform, washed 3 times with water, each time with 40 parts by volume, and dried over sodium sulfate. After evaporation of the solvent in vacuo, there is isolated 21.0 parts by weight of 2-chloro-2',6'-dimethyl-N-(1,2,4-triazol-1-yl-methyl)-acetanilide, m.p.: 115°–118° C.; after recrystallization from ethanol, it melts at 120° C.

| $C_{13}H_{15}ClN_4O$ (molecular weight: 279) | | | |
|---|---|---|---|
| | C | H | N |
| calc.: | 56.0 | 5.4 | 20.1 |
| found: | 56.2 | 5.6 | 19.7 |

EXAMPLE 2

43.9 parts by weight of 2-chloro-2',6'-dimethyl-N-chloromethyl acetanilide and 25.8 parts by weight of pyrazole are stirred for 7 hours at 90° C. in 120 parts by volume of toluene. After the mixture has cooled it is filtered, and the filtrate is washed 3 times with water, each time with 50 parts by volume, and dried over sodium sulfate. The solvent is evaporated and the residue pasted with 50 parts by volume of petroleum ether to give 39.1 parts by weight of 2-chloro-2',6'-dimethyl-N-(pyrazol-1-yl-methyl)-acetanilide, m.p.: 81° C.

| $C_{14}H_{16}ClN_3O$ (molecular weight: 278) | | | |
|---|---|---|---|
| | C | H | N |
| calc.: | 60.5 | 5.8 | 15.1 |
| found: | 60.7 | 5.8 | 14.7 |

EXAMPLE 3

68.5 parts by weight of 2-chloro-2',6'-diethyl-N-chloromethyl acetanilide and 50.4 parts by weight of 3,5-dimethylpyrazole are stirred in 100 parts by volume of toluene for 8 hours at from 90° to 95° C. After the mixture has cooled to room temperature, it is filtered, and the filtrate is washed 3 times with water, each time with 100 parts by volume, and dried over sodium sulfate. After evaporation of the solvent in vacuo, 42.5 parts by weight of 2-chloro-2',6'-diethyl-N-(3,5-dimethylpyrazol-1-yl-methyl)-acetanilide (m.p. 107°–109° C.) is isolated by pasting the residue with 70 parts by volume of petroleum ether.

| $C_{18}H_{24}ClN_3O$ (molecular weight: 334) | | | |
|---|---|---|---|
| | C | H | N |
| calc.: | 64.8 | 7.2 | 12.6 |
| found: | 64.6 | 7.2 | 12.5 |

EXAMPLE 4

21.4 parts by weight of 2-chloro-2'-methyl-6'-ethyl-N-chloromethyl acetanilide and 20.2 parts by weight of 4-chloro-3,5-dimethylpyrazole are refluxed for 10 hours in 100 parts by volume of glycol dimethyl ether. After cooling the mixture to 0° C., it is filtered, and the filtrate, concentrated to 23.8 parts by weight, is filtered with 600 parts by volume of chloroform through 50 parts by weight of silica gel. From the concentrated chloroform filtrate there is isolated 20.4 parts by weight of 2-chloro-2'-methyl-6'-ethyl-N-(4-chloro-3,5-dimethylpyrazol-1-yl-methyl)-acetanilide as an oil which completely crystallizes upon milling with 50 ml of petroleum ether (m.p. 66° C. from petroleum ether).

| $C_{17}H_{21}Cl_2N_3O$ (molecular weight: 354) | | | |
|---|---|---|---|
| | C | H | N |
| calc.: | 57.6 | 6.0 | 11.9 |
| found: | 57.8 | 6.0 | 11.5 |

EXAMPLE 5

28.5 parts by weight of 2-chloro-N-chloromethyl-2'-methyl-6'-ethyl acetanilide and 17.4 parts by weight of 3(5)-methyl-1,2,4-triazole are refluxed for 6 hours in 150 parts by volume of anhydrous tetrahydrofuran. After the mixture has cooled to 0° C., it is filtered, the filtrate is concentrated in vacuo, and the residue is thoroughly milled with 200 parts by volume of water, suction filtered and dried. There is obtained 20.5 parts by weight of 2-chloro-2'-methyl-6'-ethyl-N-(3(5)-methyl-1,2,4-triazol-1-yl-methyl)-acetanilide as a crystalline powder (m.p. 89°–91° C.), which melts at 90° to 93° C. after recrystallization from a 3:1 mixture of toluene and petroleum ether; the 3(5)-position isomer ratio is 3:1.

| $C_{15}H_{19}ClN_4O$ (molecular weight: 306.5) | | | |
|---|---|---|---|
| | C | H | N |
| calc.: | 58.7 | 6.2 | 18.3 |
| found: | 58.8 | 6.3 | 17.9 |

EXAMPLE 6

3.5 parts by weight of 1,2,4-triazole is dissolved in 8.8 parts by weight of 30% strength sodium methylate solution; the resulting solution is evaporated to dryness in vacuo at 50° C. This crystalline residue is introduced in portions into a solution of 13.0 parts by weight of 2-chloro-2'-methyl-6'-ethyl-N-chloromethyl acetanilide in 80 parts by volume of anhydrous acetonitrile, while stirring and at room temperature. After 24 hours the undissolved matter is filtered off and the filtrate is concentrated in vacuo. The residue is filtered with 300 parts by volume of chloroform through 60 parts by weight of silica gel to give, after evaporation of the eluate, 8.0 parts by weight of 2-chloro-2'-methyl-6'-ethyl-N-(1,2,4-triazol-1-yl-methyl)-acetanilide; m.p.: 84° C.

| $C_{14}H_{17}ClN_4O$ (molecular weight: 293) | | | |
|---|---|---|---|
| | C | H | N |
| calc.: | 57.4 | 5.9 | 19.1 |
| found: | 57.9 | 6.0 | 18.6 |

EXAMPLE 7

At 25° to 30° C. 6.5 parts of sodium azide is introduced in portions into a solution of 26.1 parts by weight of 2-chloro-2'-methyl-6'-ethyl-N-chloromethyl acetanilide in 100 parts of anhydrous dimethylformamide, and the whole is stirred for 2 hours. After the addition of 200 parts by volume of water, the organic phase is separated, taken up in 200 parts by volume of methylene chloride, washed 3 times with water, each time with 50 parts by volume, and dried over sodium sulfate. After filtration, 14.2 parts by volume of the dimethyl ester of acetylenedicarboxylic acid is dripped in, the temperature rising to 30° C. After 2 hours, the mixture is concentrated in vacuo. From the residue there is obtained, after milling with methanol, 21.5 parts by weight of 2-chloro-2'-methyl-6'-ethyl-N-(4,5-bis-carbomethoxy-1,2,3-triazol-1-yl-methyl)-acetanilide; m.p.: 103°–105° C.

EXAMPLE 8

10.0 parts by weight of 2-chloro-2'-methyl-6'-ethyl-N-(1,2,4-triazol-1-yl-methyl)-acetanilide is dissolved in 50 parts by volume of a mixture of anhydrous dichloromethane and ether (1:1). Dry hydrogen chloride is then passed in, while cooling, for 15 minutes, and a further 55 parts by volume of anhydrous ether is dripped in. The precipitated crystals are suction filtered, and there is obtained 7.5 parts by weight of 2-chloro-2'-methyl-6'-ethyl-N-(1,2,4-triazol-1-yl-methyl)acetanilide hydrochloride; m.p.: 148° C.

| $C_{14}H_{18}Cl_2N_4O$ (molecular weight: 329) | | | |
|---|---|---|---|
| | C | H | N |
| calc.: | 51.1 | 5.5 | 17.0 |
| found: | 51.4 | 5.6 | 17.0 |

The following compounds are obtained analogously:

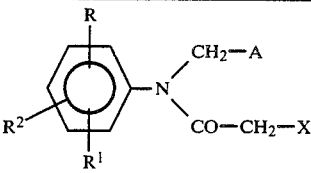

| No. | R | R¹ | R² | X | A | m.p. (°C.) |
|---|---|---|---|---|---|---|
| 1 | H | H | H | Cl | 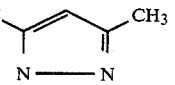 | 98 |
| 2 | 2-CH₃ | H | H | Cl | " | oil |
| 3 | 2-C₂H₅ | H | H | Cl | " | oil |
| 4 | 2-CH(CH₃)₂ | H | H | Cl | " | 54 |
| 5 | 2-CH₃ | 6-CH₃ | H | Cl | " | 81 |
| 6 | 2-CH₃ | 6-C₂H₅ | H | Br | " | |
| 7 | 2-C₂H₅ | 6-CH₃ | H | Cl | " | 56 |
| 8 | 2-C₂H₅ | 6-C₂H₅ | H | Cl | " | 68 |
| 9 | 6-CH₃ | 2-CH(CH₃)₂ | H | Cl | " | 91 |
| 10 | 6-CH₃ | 2-C(CH₃)₃ | H | Cl | " | |
| 11 | 2-CH(CH₃)₂ | 6-CH(CH₃)₂ | H | Cl | " | 132 |
| 12 | 2-CH₃ | 6-CH₃ | H | Br | " | |
| 13 | 2-CH₃ | 6-CH₃ | 4-CH₃ | Cl | " | 92 |
| 14 | 2-CH₃ | 6-CH₃ | 3-CH₃ | Cl | " | 84 |
| 15 | 2-CH₃ | 6-C₂H₅ | 4-CH₃ | Cl | " | |
| 16 | 5-CH₃ | 4-CH₃ | 2-CH₃ | Cl | " | |
| 17 | H | 2-CH₃ | 3-CH₃ | Cl | " | 102 |
| 18 | H | 2-CH₃ | 4-CH₃ | Cl | " | oil |
| 19 | H | 2-CH₃ | 5-CH₃ | Cl | " | oil |
| 20 | H | 2-CH₃ | 4-CH₃O | Cl | " | 100 |
| 21 | 6-CH₃ | 3-CH₃ | 4-CH₃O | Cl | " | |
| 22 | 2-CH₃ | 3-CH₃ | 4-CH₃O | Cl | " | oil |
| 23 | H | 2-CH₃ | 4-Cl | Cl | " | |
| 24 | 2-CH₃ | H | 5-Cl | Cl | " | oil |
| 25 | 6-Cl | 2-CH₃ | H | Cl | " | |
| 26 | H | 3-Cl | H | Cl | " | 125 |
| 27 | H | 3-Cl | 5-Cl | Cl | " | 126 |
| 28 | 6-Cl | 2-Cl | H | Cl | " | |
| 29 | 4-CH₃O | 3-Cl | 2-CH₃ | Cl | " | |
| 30 | H | 2,3-(CH₂)₃ | | Cl | " | |
| 31 | H | 2,3-(CH₂)₄ | | Cl | " | |
| 32 | 6-CH₃ | 2,3-(CH₂)₃ | | Cl | " | |
| 33 | H | 3,4-(CH₂)₃ | | Cl | " | oil |
| 34 | H | H | H | Cl | H₃C—C=C—CH₃ in N—N ring | 90 |
| 35 | 2-CH₃ | H | H | Cl | " | 94 |
| 36 | 2-C₂H₅ | H | H | Cl | " | 121 |
| 37 | 2-CH(CH₃)₂ | H | H | Cl | " | 129 |
| 38 | 2-CH₃ | 6-CH₃ | H | Cl | " | 126 |
| 39 | 2-CH₃ | 6-C₂H₅ | H | Br | " | |
| 40 | 2-C₂H₅ | 6-CH₃ | H | Cl | " | 89-91 |
| 41 | 2-C₂H₅ | 6-C₂H₅ | H | Cl | " | 107-9 |
| 42 | 6-CH₃ | 2-CH(CH₃)₂ | H | Cl | " | 131 |
| 43 | 6-CH₃ | 2-CH(CH₃)₃ | H | Cl | " | |
| 44 | 2-CH(CH₃)₂ | 6-CH(CH₃)₂ | H | Cl | " | 128 |
| 45 | 2-CH₃ | 6-CH₃ | H | Br | " | |
| 46 | 2-CH₃ | 6-CH₃ | 4-CH₃ | Cl | " | 100 |
| 47 | 2-CH₃ | 6-CH₃ | 3-CH₃ | Cl | " | 98 |
| 48 | 2-CH₃ | 6-C₂H₅ | 4-CH₃ | Cl | " | |
| 49 | 5-CH₃ | 4-CH₃ | 2-CH₃ | Cl | " | |
| 50 | H | 2-CH₃ | 3-CH₃ | Cl | " | 129 |
| 51 | H | 2-CH₃ | 4-CH₃ | Cl | " | viscous mass |
| 52 | H | 2-CH₃ | 5-CH₃ | Cl | " | 86 |
| 53 | H | 2-CH₃ | 4-CH₃O | Cl | " | oil |
| 54 | 6-CH₃ | 3-CH₃ | 4-CH₃O | Cl | " | |
| 55 | 2-CH₃ | 3-CH₃ | 4-CH₃O | Cl | " | 138 |
| 56 | H | 2-CH₃ | 4-Cl | Cl | " | |
| 57 | H | 2-CH₃ | 5-Cl | Cl | " | 138 |
| 58 | 6-Cl | 2-CH₃ | H | Cl | " | |
| 59 | H | 3-Cl | 5-Cl | Cl | " | |
| 60 | 6-Cl | 2-Cl | H | Cl | " | |

-continued

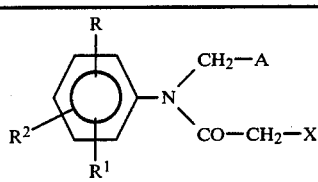

| No. | R | R¹ | R² | X | A | m.p. (°C.) |
|---|---|---|---|---|---|---|
| 61 | 4-CH$_3$O | 3-Cl | 2-CH$_3$ | Cl | " | |
| 62 | H | 3-CF$_3$ | H | Cl | " | 102 |
| 63 | H | | 2,3-(CH$_2$)$_3$ | Cl | " | |
| 64 | H | | 2,3-(CH$_2$)$_4$ | Cl | " | |
| 65 | 6-CH$_3$ | | 2,3-(CH$_2$)$_3$ | Cl | " | |
| 66 | H | | 3,4-(CH$_2$)$_3$ | Cl | " | 105 |
| 67 | 2-CH$_3$ | 6-CH$_3$ | H | Cl | (pyrazole with CH$_3$) | 63–66 |
| 68 | 2-CH$_3$ | 6-C$_2$H$_5$ | H | Cl | " | oil |
| 69 | 2-C$_2$H$_5$ | H | H | Cl | " | oil |
| 70 | 2-C$_2$H$_5$ | 2-C$_2$H$_5$ | H | Cl | " | 90–94 |
| 71 | 2-CH$_3$ | 2-CH(CH$_3$)$_2$ | H | Cl | " | |
| 72 | 2-CH(CH$_3$)$_2$ | H | H | Cl | " | oil |
| 73 | 2-CH$_3$ | 6-CH$_3$ | H | Cl | (pyrazole with CH$_3$) | 102 |
| 74 | 2-CH$_3$ | 6-C$_2$H$_5$ | H | Cl | " | 72 |
| 75 | 2-C$_2$H$_5$ | 6-C$_2$H$_5$ | H | Cl | " | |
| 76 | 2-CH$_3$ | 6-CH(CH$_3$)$_2$ | H | Cl | " | |
| 77 | H | H | H | Cl | (trimethyl pyrazole) | 114 |
| 78 | 2-CH$_3$ | H | H | Cl | " | 82 |
| 79 | 2-C$_2$H$_5$ | H | H | Cl | " | 78 |
| 80 | 2-CH(CH$_3$)$_2$ | H | H | Cl | " | 143 |
| 81 | 2-CH$_3$ | 6-CH$_3$ | H | Cl | " | oil |
| 82 | 2-CH$_3$ | 6-C$_2$H$_5$ | H | Cl | " | |
| 83 | 2-C$_2$H$_5$ | 6-C$_2$H$_5$ | H | Cl | " | |
| 84 | 2-CH$_3$ | 6-C$_2$H$_5$ | H | Cl | (acetyl pyrazole) | 143 |
| 85 | 2-C$_2$H$_5$ | 6-C$_2$H$_5$ | H | Cl | " | 85 |
| 86 | H | H | H | Cl | (phenyl pyrazole) | 115 |
| 87 | 2-CH$_3$ | 6-CH$_3$ | H | Cl | " | 150 |
| 88 | 2-CH$_3$ | 6-C$_2$H$_5$ | H | Cl | " | 132 |
| 89 | 2-C$_2$H$_5$ | 6-C$_2$H$_5$ | H | Cl | " | 99 |
| 90 | 2-CH$_3$ | 6-CH$_3$ | H | Cl | (diphenyl pyrazole) | |
| 91 | 2-CH$_3$ | 6-C$_2$H$_5$ | H | Cl | " | 145 |

-continued

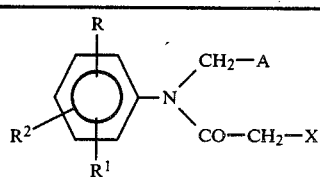

| No. | R | R¹ | R² | X | A | m.p. (°C.) |
|---|---|---|---|---|---|---|
| 92 | 2-CH₃ | 6-CH₃ | H | Cl | (1-phenyl-2-methyl pyrazole group) | 115 |
| 93 | 2-CH₃ | 6-C₂H₅ | H | Cl | " | 125 |
| 94 | 2-C₂H₅ | 6-C₂H₅ | H | Cl | " | 126 |
| 95 | 2-CH₃ | 6-CH₃ | H | Cl | (4-chloropyrazole) | 104 |
| 96 | 2-CH₃ | 6-C₂H₅ | H | Cl | " | 94 |
| 97 | 2-C₂H₅ | 6-C₂H₅ | H | Cl | " | 111 |
| 98 | 2-CH₃ | 6-CH(CH₃)₂ | H | Cl | " | |
| 99 | 2-CH₃ | 6-CH₃ | H | Cl | (4-bromopyrazole) | 102 |
| 100 | 2-CH₃ | 6-C₂H₅ | H | Cl | " | 80 |
| 101 | 2-C₂H₅ | 6-C₂H₅ | H | Cl | " | 113 |
| 102 | 2-CH₃ | 6-CH₃ | H | Cl | (4-iodopyrazole) | |
| 103 | 2-CH₃ | 6-CH₃ | H | Cl | (3,4,5-trichloropyrazole) | |
| 104 | 2-CH₃ | 6-C₂H₅ | H | Cl | " | |
| 105 | H | H | H | Cl | (4-chloro-3,5-dimethylpyrazole) | 111 |
| 106 | 2-CH₃ | 6-CH₃ | H | Cl | " | 105 |
| 107 | 2-CH₃ | 6-C₂H₅ | H | Cl | " | 63–66 |
| 108 | 2-C₂H₅ | 6-C₂H₅ | H | Cl | " | 88 |
| 109 | 2-CH₃ | 6-CH₃ | H | Cl | (4-chloro-3-methylpyrazole) | |
| 110 | 2-CH₃ | 6-C₂H₅ | H | Cl | " | |
| 111 | 2-C₂H₅ | 6-C₂H₅ | H | Cl | " | |
| 112 | 2-CH₃ | 6-CH₃ | H | Cl | (3,5-dichloro-4-methylpyrazole) | |

-continued

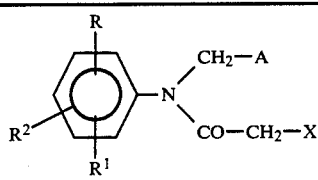

| No. | R | R¹ | R² | X | A | m.p. (°C.) |
|---|---|---|---|---|---|---|
| 113 | 2-$CH_3$ | 6-$CH_3$ | H | Cl | $CH_3O$–C=CH–C($CH_3$)=N–N (pyrazole) | oil |
| 114 | 2-$CH_3$ | 6-$C_2H_5$ | H | Cl | " | |
| 115 | 2-$CH_3$ | 6-$CH_3$ | H | Cl | $F_3C$–C=CH–C($CH_3$)=N–N (pyrazole) | |
| 116 | 2-$CH_3$ | 6-$CH_3$ | H | Cl | $CF_3$–C=CH–C($CF_3$)=N–N (pyrazole) | 130 |
| 117 | 2-$CH_3$ | 6-$C_2H_5$ | H | Cl | " | |
| 118 | 2-$C_2H_5$ | 6-$C_2H_5$ | H | Cl | " | |
| 119 | 2-$CH_3$ | 6-$CH(CH_3)_2$ | H | Cl | " | |
| 120 | 2-$CH_3$ | 6-$CH_3$ | H | Cl | $H_3C$–C=CH–C($CO_2C_2H_5$)=N–N (pyrazole) | |
| 121 | 2-$CH_3$ | 6-$CH_3$ | H | Cl | $H_5C_2O_2C$–C=CH–C($CO_2C_2H_5$)=N–N (pyrazole) | |
| 122 | 2-$CH_3$ | 6-$CH_3$ | H | Cl | Cl–C=C($OCH_3$)–C(Cl)=N–N (pyrazole) | |
| 123 | 2-$CH_3$ | 6-$CH_3$ | H | Cl | pyrazole·$CF_3SO_3H$ | |
| 124 | H | H | H | Cl | 1,2,4-triazol-1-yl | 139 |
| 125 | 2-$C_2H_5$ | H | H | Cl | " | 94 |
| 126 | 2-$CH(CH_3)_2$ | H | H | Cl | " | 116 |
| 127 | 2-$CH_3$ | 6-$CH_3$ | H | Cl | " | 120 |
| 128 | 2-$CH_3$ | 6-$C_2H_5$ | H | Br | " | |
| 129 | 2-$C_2H_5$ | 6-$CH_3$ | H | Cl | " | 84 |
| 130 | 2-$C_2H_5$ | 6-$C_2H_5$ | H | Cl | " | 114 |
| 131 | 6-$CH_3$ | 2-$CH(CH_3)_2$ | H | Cl | " | 128 |
| 132 | 6-$CH_3$ | 2-$C(CH_3)_3$ | H | Cl | " | |
| 133 | 2-$CH(CH_3)_2$ | 6-$CH(CH_3)_2$ | H | Cl | " | 126 |
| 134 | 2-$CH_3$ | 6-$CH_3$ | H | Br | " | |
| 135 | 2-$CH_3$ | 6-$CH_3$ | 4-$CH_3$ | Cl | " | 90 |
| 136 | 2-$CH_3$ | 6-$CH_3$ | 3-$CH_3$ | Cl | " | 105 |
| 137 | 2-$CH_3$ | 6-$C_2H_5$ | 4-$CH_3$ | Cl | " | |
| 138 | 5-$CH_3$ | 4-$CH_3$ | 2-$CH_3$ | Cl | " | |
| 139 | H | 2-$CH_3$ | 3-$CH_3$ | Cl | " | 118 |
| 140 | H | 2-$CH_3$ | 4-$CH_3$ | Cl | " | viscous mass |
| 141 | H | 2-$CH_3$ | 5-$CH_3$ | Cl | " | 88 |
| 142 | H | 2-$CH_3$ | 4-$CH_3O$ | Cl | " | |
| 143 | 6-$CH_3$ | 3-$CH_3$ | 4-$CH_3O$ | Cl | " | 114 |
| 144 | 2-$CH_3$ | 3-$CH_3$ | 4-$CH_3O$ | Cl | " | oil |
| 145 | H | 2-$CH_3$ | 4-Cl | Cl | " | |
| 146 | H | 2-$CH_3$ | 5-Cl | Cl | " | 122 |

-continued

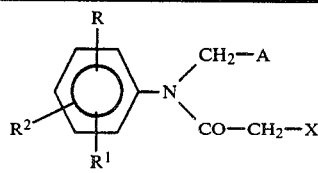

| No. | R | R¹ | R² | X | A | m.p. (°C.) |
|---|---|---|---|---|---|---|
| 147 | 6-Cl | 2-CH₃ | H | Cl | " | |
| 148 | H | 3-Cl | H | Cl | " | 107 |
| 149 | H | 3-Cl | 4-Cl | Cl | " | 146 |
| 150 | H | 3-Cl | 5-Cl | Cl | " | 151 |
| 151 | 6-Cl | 2-Cl | H | Cl | " | |
| 152 | 4-CH₃O | 3-Cl | 2-CH₃ | Cl | " | |
| 153 | H | 2,3-(CH₂)₃ | | Cl | " | |
| 154 | H | 2,3-(CH₂)₄ | | Cl | " | |
| 155 | 6-CH₃ | 2,3-(CH₂)₃ | | Cl | " | |
| 156 | H | 3,4-(CH₂)₃ | | Cl | " | 124 |
| 157 | 2-CH₃ | 6-CH₃ | H | Cl | (triazole-CH₃) | 158 |
| 158 | 2-CH₃ | 6-C₂H₅ | H | Cl | " | 90–93 |
| 159 | 2-C₂H₅ | 6-C₂H₅ | H | Cl | " | 122–24 |
| 160 | 2-CH₃ | 6-CH₃ | H | Cl | (H₃C-triazole-CH₃) | 131 |
| 161 | 2-C₂H₅ | 6-CH₃ | H | Cl | " | 85 |
| 162 | 2-C₂H₅ | 6-C₂H₅ | H | Cl | " | 71–73 |
| 163 | 2-CH₃ | 6-CH₃ | H | Cl | (triazole-Cl) | |
| 164 | 2-CH₃ | 6-C₂H₅ | H | Cl | " | |
| 165 | 2-CH₃ | 6-CH₃ | H | Cl | (H₃C-triazole-Cl) | |
| 166 | 2-C₂H₅ | 6-CH₃ | H | Cl | " | |
| 167 | 2-CH₃ | 6-CH₃ | H | Cl | (Cl-triazole-Cl) | |
| 168 | 2-CH₃ | 6-CH₃ | H | Cl | (NC-triazole-Cl) | |
| 169 | 2-CH₃ | 6-CH₃ | H | Cl | (Ph-triazole-Cl) | |
| 170 | 2-CH₃ | 6-CH₃ | H | Cl | (H₅C₂O₂C-triazole-Cl) | |

-continued

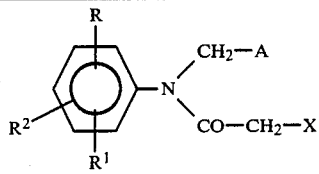

| No. | R | R¹ | R² | X | A | m.p. (°C.) |
|---|---|---|---|---|---|---|
| 171 | 2-CH₃ | 6-CH₃ | H | Cl | (1,2,3-triazole) | |
| 172 | 2-CH₃ | 6-C₂H₅ | H | Cl | " | 103–104 |
| 173 | 2-C₂H₅ | 6-C₂H₅ | H | Cl | " | |
| 174 | 2-CH₃ | 6-CH(CH₃)₂ | H | Cl | " | |
| 175 | 2-CH₃ | 6-CH₃ | H | Cl | H₃C-(triazole) | |
| 176 | 2-CH₃ | 6-CH₃ | H | Cl | (H₃C)(H₃C)-triazole | |
| 177 | 2-CH₃ | 6-C₂H₅ | H | Cl | " | |
| 178 | 2-C₂H₅ | 6-C₂H₅ | H | Cl | " | |
| 179 | 2-CH₃ | 6-CH₃ | H | Cl | Ph-triazole | |
| 180 | 2-CH₃ | 6-CH₃ | H | Cl | Cl-triazole | |
| 181 | 2-CH₃ | 6-C₂H₅ | H | Cl | H₃CO₂C-triazole | oil |
| 182 | 2-CH₃ | 6-C₂H₅ | H | Cl | (HO₂C)(HO₂C)-triazole | 162 |
| 183 | 2-CH₃ | 6-CH₃ | H | Cl | H₅C₂O₂C-triazole | |
| 184 | 2-CH₃ | 6-C₂H₅ | H | Cl | (H₃CO₂C)(H₃CO₂C)-triazole | 103–105 |
| 185 | 2-CH₃ | 6-C₂H₅ | H | Cl | ((CH₃)₂HCO₂C)((CH₃)₂HCO₂C)-triazole | 94 |
| 186 | 2-CH₃ | 6-CH₃ | H | Cl | H₃C-tetrazole | |
| 187 | 2-CH₃ | 6-CH₃ | H | Cl | H₅C₂O₂C-tetrazole | |

-continued

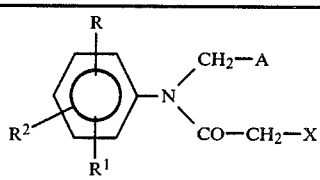

| No. | R | R¹ | R² | X | A | m.p. (°C.) |
|---|---|---|---|---|---|---|
| 188 | 2-CH₃ | 6-CH₃ | H | Cl | [1,2,4-triazole].HCl | |
| 189 | 2-CH₃ | 6-C₂H₅ | H | Cl | " | 148 |
| 190 | 2-CH₃ | 6-CH₃ | H | Cl | [1,2,4-triazole].H₂SO₄ | |
| 191 | 2-CH₃ | 6-C₂H₅ | H | Cl | [1,2,4-triazole].HNO₃ | 145 |
| 192 | 2-CH₃ | 6-CH₃ | H | Cl | [1,2,4-triazole].HBr | |
| 193 | 2-CH₃ | 6-CH₃ | H | Cl | [1,2,4-triazole].CH₃SO₃H | |
| 194 | 2-CH₃ | 6-CH₃ | H | Cl | [1,2,4-triazole].CF₃SO₃H | |
| 195 | 2-CH₃ | 6-C₂H₅ | H | Cl | [1,2,4-triazole].C₁₂H₂₅–C₆H₄–SO₃H | 133–135 |
| 196 | 2-CH₃ | 6-C₂H₅ | H | Cl | [1,2,3-triazole].HCl | |
| 197 | 2-CH₃ | 6-C₂H₅ | H | Cl | [1,2,3-triazole].C₁₂H₂₅–C₆H₄–SO₃H | |
| 198 | 2-CH₃ | 6-CH₃ | H | Cl | 4-(CH(CH₃)₂)-pyrazole | 58 |
| 199 | 2-CH₃ | 6-C₂H₅ | H | Cl | " | 67 |
| 200 | 2-CH₃ | 6-CH₃ | H | Cl | 4-OCH₃-pyrazole | 118 |
| 201 | 2-CH₃ | 6-C₂H₅ | H | Cl | " | 94 |
| 202 | 2-C₂H₅ | 6-C₂H₅ | H | Cl | " | 94 |

-continued structure:
R, R² on phenyl ring with R¹; N substituted with CH₂—A and CO—CH₂—X

| No. | R | R¹ | R² | X | A | m.p. (°C.) |
|---|---|---|---|---|---|---|
| 203 | 2-CH₃ | 6-CH₃ | H | Cl | 1,2,3-triazol-1-yl (N—N=N, CH=N) | 108–112 |
| 204 | 2-CH₃ | 6-CH₃ | H | Cl | imidazol-1-yl | 127 |
| 205 | 2-CH₃ | 6-C₂H₅ | H | Cl | " | 106 |
| 206 | 2-CH₃ | 6-CH₃ | H | Cl | 2-methylimidazol-1-yl | 116 |
| 207 | 2-CH₃ | 6-CH₃ | H | Cl | 4,5-dichloroimidazol-1-yl | 95 |
| 208 | 2-CH₃ | 6-C₂H₅ | H | Cl | " | 88 |
| 209 | 2-C₂H₅ | 6-C₂H₅ | H | Cl | " | 104 |
| 210 | 2-CH₃ | 6-C₂H₅ | H | Cl | 2,4,5-trichloroimidazol-1-yl | 162 |
| 211 | 2-CH₃ | 6-CH₃ | H | Cl | 4,5-dichloro-2-methylimidazol-1-yl | 170 |
| 212 | 2-CH₃ | 6-C₂H₅ | H | Cl | " | 165 |
| 213 | 2-CH₃ | 2-CH₃ | H | Cl | 4,5-dichloro-2-ethylimidazol-1-yl | 114 |
| 214 | 2-CH₃ | 6-C₂H₅ | H | Cl | " | 100 |
| 215 | 2-CH₃ | 6-CH₃ | H | Cl | 4,5-dichloro-2-isopropylimidazol-1-yl | 161 |
| 216 | 2-CH₃ | 6-C₂H₅ | H | Cl | " | 112 |
| 217 | 2-CH₃ | 6-CH₃ | H | Cl | 2,4,5-tribromoimidazol-1-yl | 168 |
| 218 | 2-CH₃ | 6-C₂H₅ | H | Cl | " | 170 |
| 219 | 2-CH₃ | 6-CH₃ | H | Cl | 2-bromo-4,5-dichloroimidazol-1-yl | 168 |

-continued $$\underset{R^1}{\underset{R^2}{\bigodot}}\!\!-\!N\!\!<\!\!\begin{array}{l}CH_2\!-\!A\\CO\!-\!CH_2\!-\!X\end{array}$$

| No. | R | R¹ | R² | X | A | m.p. (°C.) |
|---|---|---|---|---|---|---|
| 220 | H | H | H | Cl | $-N{\small\begin{array}{c}N=\\ \diagdown\\ \diagup\\ CH_3\end{array}}$ | |
| 221 | 2-CH₃ | H | H | Cl | $-N{\small\begin{array}{c}N=\\ \diagdown\\ \diagup\\ CH_3\end{array}}$ | |
| 222 | H | H | H | Cl | $-N{\small\begin{array}{c}N=\!\!-Ph\\ \diagdown\\ \diagup\\ CH_3\end{array}}$ | |
| 223 | H | H | H | Cl | $-N{\small\begin{array}{c}H_3C\diagdown\\ \diagup N\\ N\!\!=\!\!\diagup\\ \diagdown SCH_3\end{array}}$ | |
| 224 | 2-CH₃ | 6-CH₃ | H | Cl | " | |
| 225 | 2-CH₃ | 6-C₂H₅ | H | Cl | | |
| 226 | 2-C₂H₅ | 6-C₂H₅ | H | Cl | " | |
| 227 | H | H | H | Cl | $-N{\small\begin{array}{c}H_3C\diagdown\\ \diagup N\\ N\!\!=\!\!\diagup\\ \diagdown CH_3\end{array}}$ | |
| 228 | 2-CH₃ | 6-C₂H₅ | H | Cl | " | |

The active ingredients according to the invention may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The new herbicidal anilides according to the invention may be mixed and jointly applied with numerous representatives of other herbicidal or growth-regulating active ingredient groups. Examples of suitable components are diazines, benzothiadiazinones, 2,6-dinitroanilines, N-phenylcarbamates, biscarbamates, thiocarbamates, halocarboxylic acids, triazines, amides, ureas, diphenyl ethers, triazinones, uracils, benzofuran derivatives, etc. Such combinations broaden the spectrum of action and often achieve synergistic effects. A number of active ingredients which, together with the new compounds, give useful compositions for the most varied areas of application, are given below:

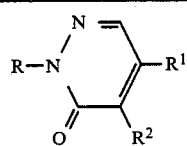

| R | $R^1$ | $R^2$ |
|---|---|---|
| 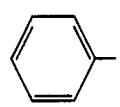 | $NH_2$ | Cl |
| 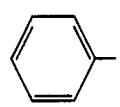 | $NH_2$ | Br |

-continued

| R | $R^1$ | $R^2$ |
|---|---|---|
| 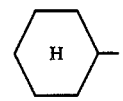 | $NH_2$ | Cl |
| 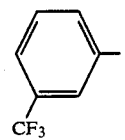 | $-N(CH_3)_2$ | Cl |
|  | $-NHCH_3$ | Cl |
| 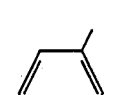 | $-NHCH_3$ | Cl |
| 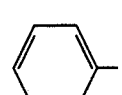 | $-N(CH_3)_2$ | Cl |

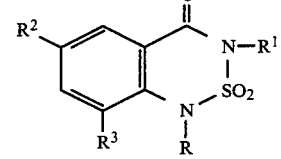

| R | $R^1$ | $R^2$ | $R^3$ | |
|---|---|---|---|---|
| H | $i$-$C_3H_7$ | H | H | or salts of this compound |
| H | $i$-$C_3H_7$ | H | $CH_3$ | or salts of this compound |
| $-CH_2-OCH_3$ | $i$-$C_3H_7$ | H | H | or salts of this compound |

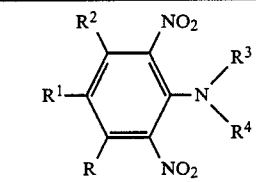

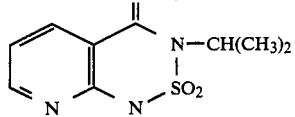

| R | $R^1$ | $R^2$ | $R^3$ | $R^4$ |
|---|---|---|---|---|
| H | $F_3C$ | H | $C_2H_5$ | $C_4H_9$ |
| H | $F_3C$ | H | $n$-$C_3H_7$ | $n$-$C_3H_7$ |
| H | $F_3C$ | H | $-CH_2-CH_2Cl$ | $n$-$C_3H_7$ |
| H | $SO_2NH_2$ | H | $n$-$C_3H_7$ | $n$-$C_3H_7$ |
| H | $F_3C$ | H | $n$-$C_3H_7$ | $-CH_2-\triangleleft$ |
| $H_3C$ | $H_3C$ | H | H | $-CH(C_2H_5)_2$ |
| H | $F_3C$ | $NH_2$ | $n$-$C_3H_7$ | $n$-$C_3H_7$ |

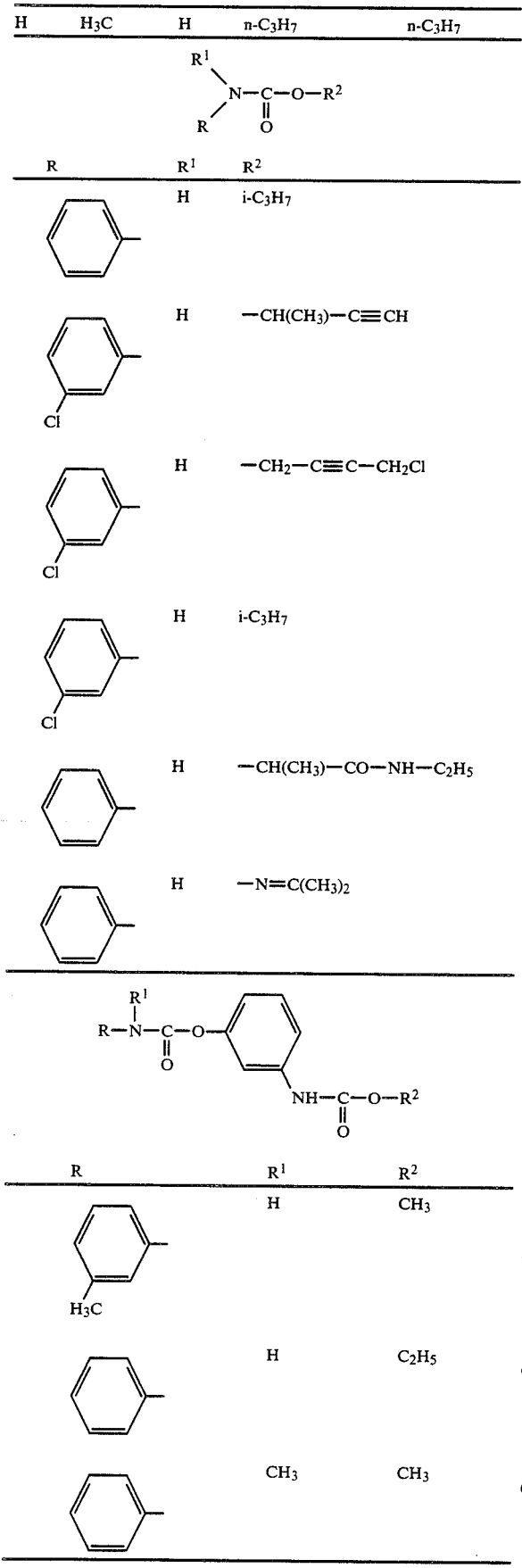
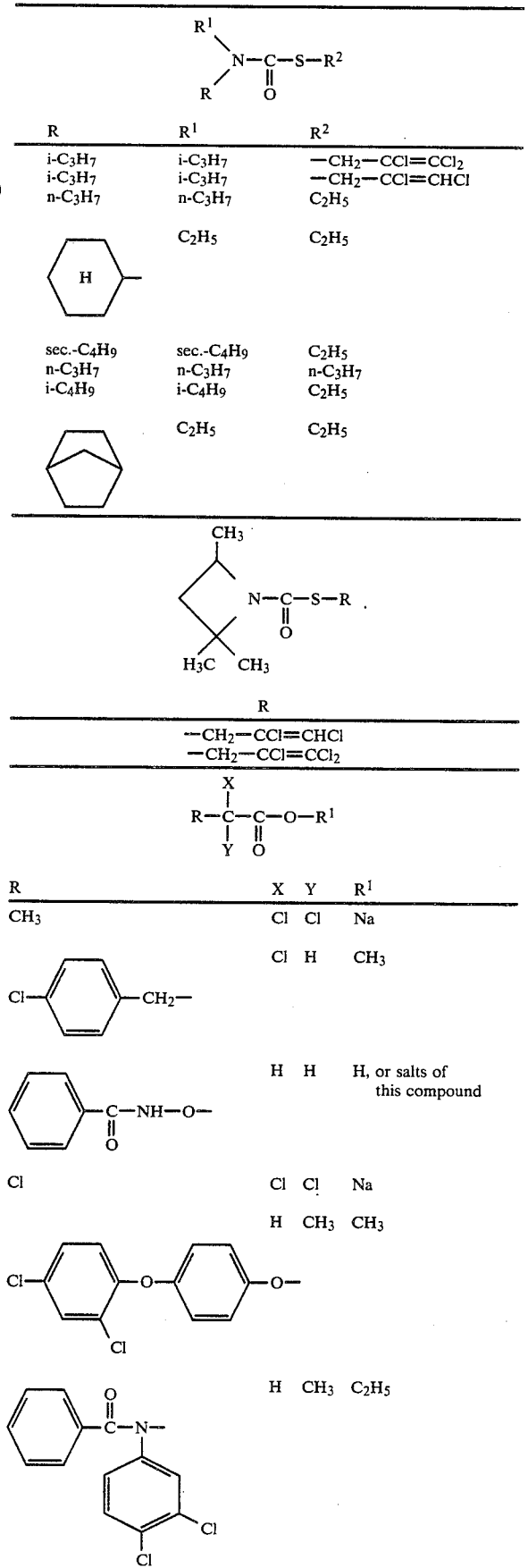

-continued

| | | | |
|---|---|---|---|
| C₂H₅ | | Cl Cl | Na |
| H | CH₃ | | i-C₃H₇ |

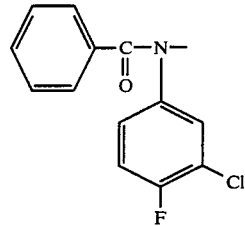

| H | CH₃ | CH₃ |

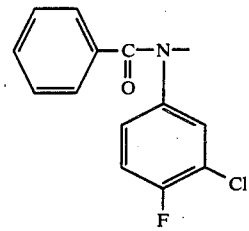

| H | CH₃ | —CH₂—CH(CH₃)₂ |

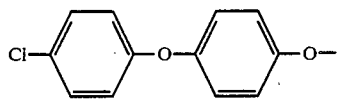

| H | CH₃ | Na |

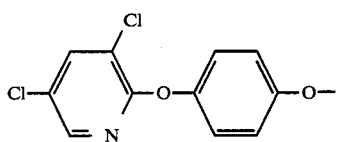

---

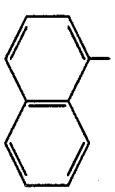

| R | R¹ | R² | R³ | X |
|---|---|---|---|---|
| H | tert.C₄H₉ | H | C₂H₅ | SCH₃ |
| H | i-C₃H₇ | H | i-C₃H₇ | SCH₃ |
| H | i-C₃H₇ | H | C₂H₅ | SCH₃ |
| H | CH₃ | H | i-C₃H₇ | SCH₃ |
| H | i-C₃H₇ | H | C₂H₅ | Cl |
| H | i-C₃H₇ | H |  | Cl |
| H | C₂H₅ | H | C₂H₅ | Cl |
| H | C₂H₅ | H | 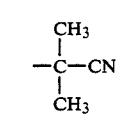 | Cl |
| H | i-C₃H₇ | H | i-C₃H₇ | Cl |
| H | i-C₃H₇ | H | i-C₃H₇ | OCH₃ |
| H | 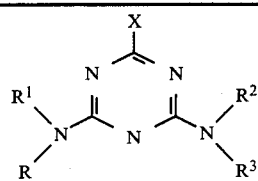 | H |  | Cl |
| H | C₂H₅ | H | —CH(CH₃)—CH₂—OCH₃ | Cl |
| H | C₂H₅ | H | —CH(CH₃)—C≡CH | Cl |

-continued

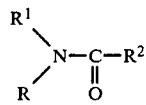

| R | R¹ | R² |
|---|---|---|
| CH₃ | CH₃ | —CH(C₆H₅)₂ |
| 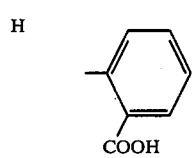 | H | 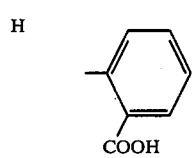 |
| C₂H₅ | C₂H₅ | 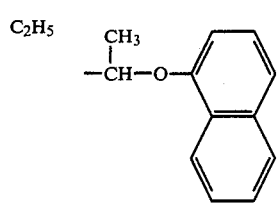 |
| HC≡C—C(CH₃)₂— | H | 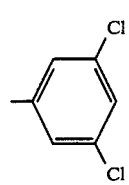 |
| 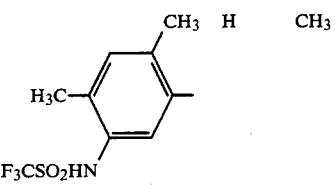 | CH₃ H | CH₃ |
| F₃CSO₂HN | | |

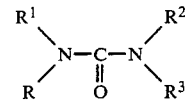

| R | R¹ | R² | R³ |
|---|---|---|---|
| | H | CH₃ | CH₃ |
| 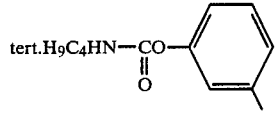 | | | |
| 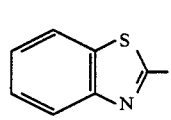 | H | CH₃ | H |
| 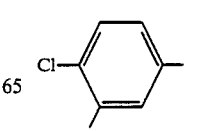 | H | CH₃ | CH₃ |

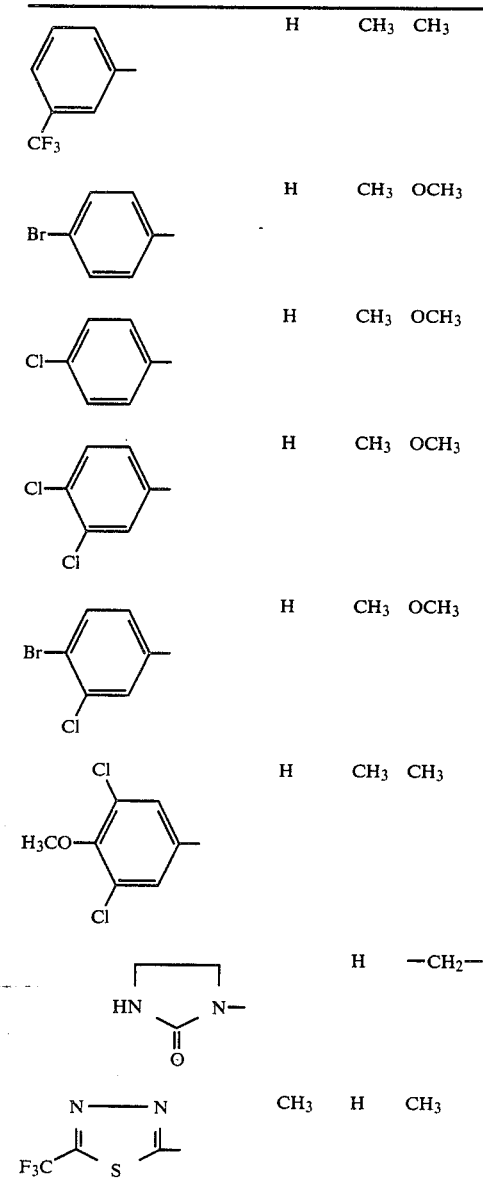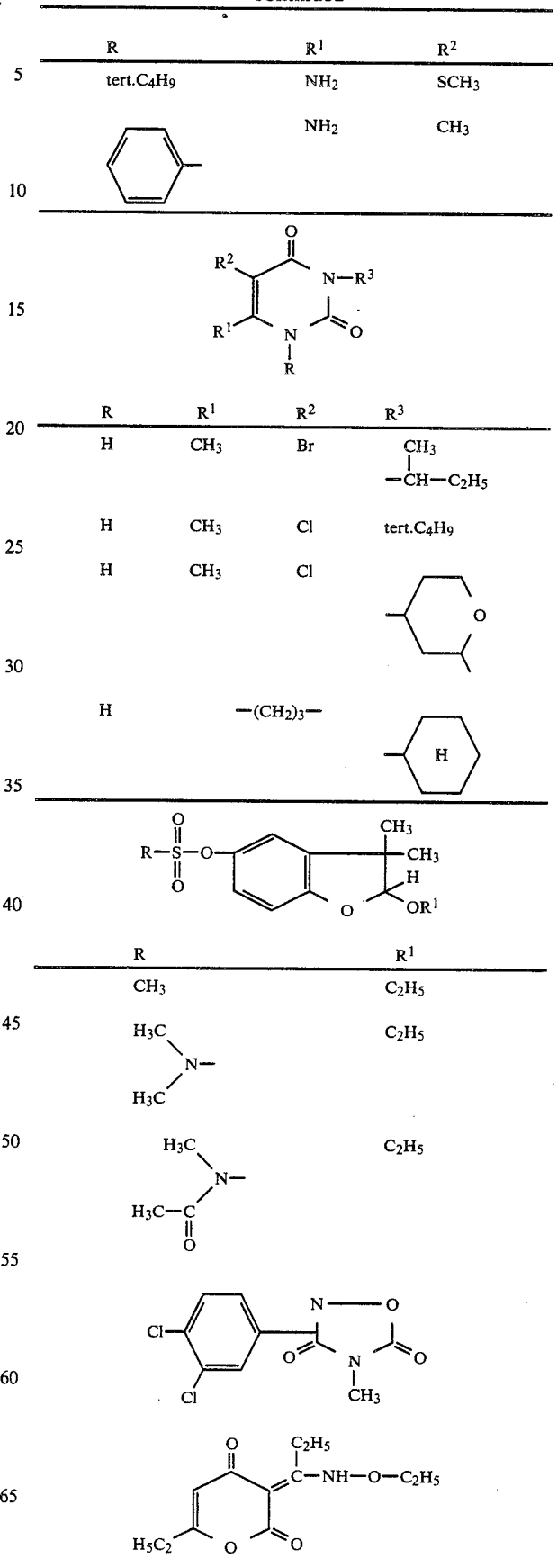

-continued

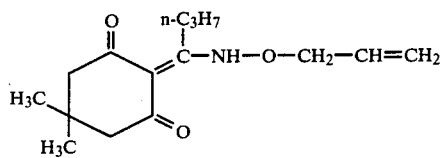

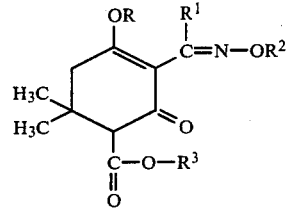

| R | R¹ | R² | R³ |
|---|---|---|---|
| H | n-C₃H₇ | —CH₂—CH=CH₂ | CH₃ |
| Na | n-C₃H₇ | —CH₂—CH=CH₂ | CH₃ | or salts or esters of this compound

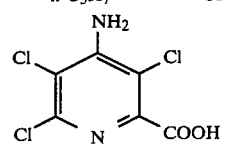

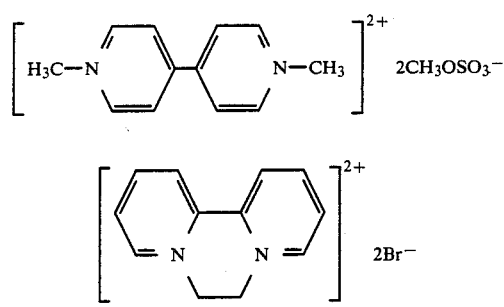

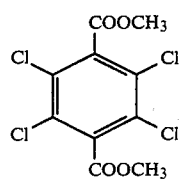

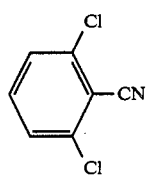

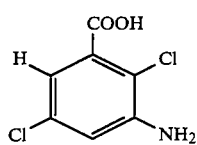

or salts, esters or amides of this compound

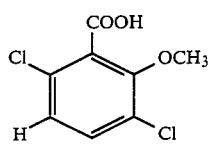

or salts, esters or amides of this compound

-continued

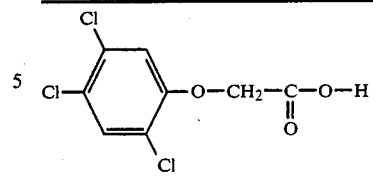

or salts, esters or amides of this compound

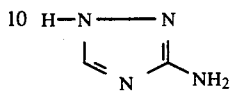

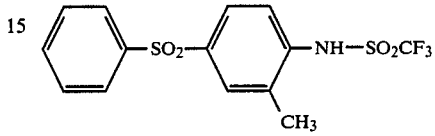

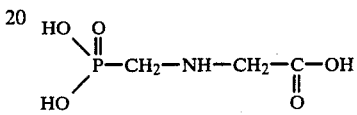

or salts of this compound

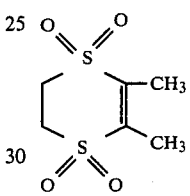

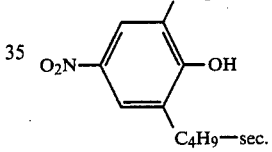

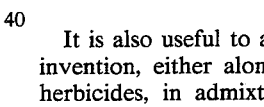

or salts of this compound

It is also useful to apply the new compounds of the invention, either alone or in combination with other herbicides, in admixture with other crop protection agents, e.g., agents for combatting pests, or phytopathogenic fungi or bacteria. Of further interest is the fact that the compounds may be mixed with mineral solutions used to eliminate nutritional and trace element deficiencies.

The influence of various representatives of the compounds of the invention on the growth of unwanted and crop plants, compared with prior art active ingredients which are chemically similar, is demonstrated in the following experiments. The series of experiments were carried out in the greenhouse and in the open.

I. Greenhouse experiments

The vessels employed were plastic flowerpots having a volume of 300 cm³; the substrate was a sandy loam containing about 1.5% humus. The seeds of the test plants (see Table 1) were sown shallow, and separated according to species. In the case of Cyperus esculentus, pregerminated tubers were planted. In the preemergence treatment, the active ingredients were then immediately applied to the surface of the soil. They were suspended or emulsified in water as the vehicle, and sprayed through atomizing nozzles. After the agents had been applied, the vessels were lightly sprinkler-irrigated to set germination and growth going, and to activate the chemical agents. The vessels were then covered with transparent plastic hoods until the plants had taken root. This cover ensured uniform germination of the test plants (to the extent that this was not impaired by the chemicals), and prevented readily volatile substances from evaporating.

For postemergence treatment, the plants were first grown to a height of from 3 to 10 cm, depending on their habit, before before treated. Hoods were not placed on the pots. The experiments were set up in the greenhouse, hotter areas (25° to 40° C.) being preferred for heat-loving species, and 15° to 30° C. for plants from moderate climates. The experiments were carried out for from 4 to 6 weeks. During this period the plants were tended and their reaction to the various treatments was assessed. The following tables contain the substances investigated, the application rates in kg/ha of active ingredient, and the test plant species. Assessments were made on a 0 to 100 scale, 0 denoting no damage or normal emergence, and 100 denoting no emergence or complete destruction of at least the visible plant parts.

II. Experiments in the open

The experiments were carried out on small plots. The soil was a sandy loam having a pH of from 5 to 6 and containing from 1 to 1.5% humus. The treatment was preemergence, the active ingredients being applied immediately or at the latest 3 days after sowing. The crop plants were sown in rows. The weed flora was made up of the most widely varying species and was natural; the weed flora depended on the time of the year and in part on the crop (e.g., spring-germinating, summer-germinating). The substances were emulsified or suspended in water as the vehicle, and applied by means of a motor-driven plot spray mounted on a hitch. When no rain fell, the plots were watered to ensure germination and growth of the crop plants and weeds. All the experiments were run for several weeks. Over this period, assessments were made at certain intervals on the 0 to 100 scale.

Results

Tables 2 to 15 contain the results.

It was astounding what a comprehensive and vehement herbicidal effect some of the anilides of the invention had on unwanted plants even at the lowest application rates (Tables 2, 10). What was also surprising was the stronger action of the new compounds on unwanted broadleaved species. In this area, too, the new active ingredients had a clear advantage over prior art compounds (Tables 3, 4, 5, 9, 10).

For crop plants there were sufficient safety margins between herbicidal action on the one hand and tolerance on the other to justify the use of the new compounds as selective herbicides (Tables 3, 5, 6, 7, 8, 9, 10, 12, 13, 14, 15).

In postemergence treatment, complete withering of the plants was possible, depending on the application rate (Table 4). When sublethal doses were given, however, growth inhibition resulted which would seem to be of interest in areas in which merely a growth-regulating action on unwanted plants is desired without their being destroyed, e.g., verges, reafforestation areas and lawns.

The herbicidal action of the new compounds is sufficiently intensive to completely destroy all herbaceous plant growth with application rates in excess of those used for selective control. Possible application areas here are the removal of unwanted plants in bush and tree crops, and in industrial plants, along railroad tracks, and on squares, playgrounds, etc.

In the tables, the application is given as pre- or postemergence. It is of course also possible for the agents to be incorporated into the soil in addition to the surface application. The agents may be incorporated before sowing, after sowing or between already established crop plants.

Another application method is post-directed or lay-by spraying. In this method, the spray is directed past the leaves of the sensitive crop plants onto the surface of the soil or the unwanted plants.

In view of the numerous application methods possible, the agents according to the invention, or compositions containing them, may be used in a large number of crop plants, in addition to those listed in the tables, for removing or inhibiting unwanted plants. The application rates may vary from 0.1 to 15 kg/ha and more, depending on the purpose for which they are used. The crop plants employed in the experiments are listed below:

TABLE 1

| Botanical name | Common name |
|---|---|
| Allium cepa | onion |
| Ananas comosus | pineapple |
| Arachis hypogaea | peanut (groundnut) |
| Asparagus officinalis | asparagus |
| Avena sativa | oats |
| Beta vulgaris spp. altissima | sugarbeet |
| Beta vulgaris spp. rapa | fodder beet |
| Beta vulgaris spp. esculenta | table beet, red beet |
| Brassica napus var. napus | rape |
| Brassica napus var. napobrassica | |
| Brassica napus var. napa | turnip |
| Brassica rapa var. silvestris | |
| Camellia sinensis | tea plant |
| Carthamus tincotius | safflower |
| Citrus limon | lemon |
| Citrus maxima | grapefruit |
| Citrus reticulata | |
| Citrus sinensis | orange |
| Coffea arabica (Coffea canephora, Coffea liberica) | coffee |
| Cucumis melo | melon |
| Cucumis sativus | cucumber |
| Cynodon dactylon | Bermudagrass in turf and lawns |
| Daucus carota | carrot |
| Elaesis guineensis | oil palm |
| Fragaria vesca | strawberry |
| Glycine max | soybean |
| Gosspyium hirsutum (Gossypium arboreum Gossypium herbaceum Gossypium vitifolium) | cotton |
| Helianthus annuus | sunflower |
| Helianthus tuberosus | |
| Hevea brasiliensis | rubber plant |
| Hordeum vulgare | barley |
| Humulus lupulus | hops |
| Ipomoea batatas | sweet potato |
| Lactuca sativa | lettuce |
| Lens culinaris | lentil |
| Linum usitatissimum | flax |
| Lycopersicon lycopersicum | tomato |
| Malus spp. | apple |
| Manihot esculenta | cassava |
| Medicago sativa | alfalfa (lucerne) |
| Mentha piperita | peppermint |
| Musa spp. | banana |
| Nicotiana tabacum (N. rustica) | tobacco |
| Olea europaea | olive |
| Oryza sativa | rice |
| Panicum miliaceum | |

TABLE 1-continued

| Botanical name | Common name |
|---|---|
| Phaseolus lunatus | limabean |
| Phaseolus mungo | mungbean |
| Phaseolus vulgaris | snapbean, green bean, dry bean |
| Pennisetum glaucum | |
| Petroselinum crispum spp. tuberosum | parsley |
| Picea abies | Norway spruce |
| Abies alba | fir |
| Pinus spp. | pine |
| Pisum sativum | English pea |
| Prunus avium | cherry |
| Prunus domestica | plum |
| Prunus persica | peach |
| Pyrus communis | pear |
| Ribes sylvestre | redcurrant |
| Ribes uva-crispa | |
| Ricinus communis | |

TABLE 1-continued

| Botanical name | Common name |
|---|---|
| Saccharum officinarum | sugar cane |
| Secale cereale | rye |
| Sesamum indicum | Sesame |
| Solanum tuberosum | Irish potato |
| Sorghum bicolor (s. vulgare) | grain sorghum |
| Sorghum dochna | |
| Spinacia oleracea | spinach |
| Theobroma cacao | cacao |
| Trifolium pratense | red clover |
| Triticum aestivum | wheat |
| Vaccinium corymbosum | blueberry |
| Vaccinium vitis-idaea | cranberry |
| Vicia faba | tick bean |
| Vigna sinensis (V. unguiculata) | cow pea |
| Vitis vinifera | grape |
| Zea mays | Indian corn, sweet corn, maize |

TABLE 2

Intensity of action of haloacetanilides on certain plants; preemergence treatment in the greenhouse Basic molecule 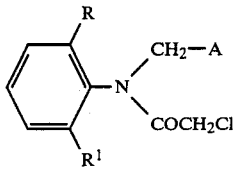

| Compound No. | Substituents R | R¹ | A | Appl. rate kg/ha | Amar. retro. | Bromus spp. | Cyp. diff. | Chrys. seget. | Euph. gen. | Poa annua | Solanum nigrum | Sorgh. halep. |
|---|---|---|---|---|---|---|---|---|---|---|---|---|
| prior art | $C_2H_5$ | $C_2H_5$ | —$OCH_3$ | 0.125 | — | 50 | 65 | — | — | 80 | — | 40 |
| | | | | 0.25 | 72 | 80 | 70 | 30 | 60 | 98 | 50 | 38 |
| prior art | $CH_3$ | $CH_3$ | (dioxolane) | 0.25 | 75 | 88 | 65 | — | — | 0 | — | 50 |
| | | | | 0.5 | 82 | 90 | 80 | 0 | 25 | 15 | 80 | 50 |
| 5 | $CH_3$ | $CH_3$ | (pyrazolyl) | 0.125 | 100 | 90 | 100 | — | — | 100 | — | 95 |
| | | | | 0.25 | 98 | 95 | 100 | 100 | 100 | 100 | 100 | 95 |
| 67 | $CH_3$ | $CH_3$ | (3-methylpyrazolyl) | 0.25 | 100 | 100 | — | — | — | — | — | 95 |
| 38 | $CH_3$ | $CH_3$ | (3,5-dimethylpyrazolyl) | 0.125 | 75 | 95 | 100 | — | — | 100 | — | 70 |
| | | | | 0.25 | 100 | 100 | 100 | — | — | 100 | — | 95 |
| 7 | $CH_3$ | $C_2H_5$ | (pyrazolyl) | 0.125 | — | — | — | — | — | — | — | — |
| | | | | 0.25 | 88 | 95 | — | 100 | 80 | 100 | 100 | 75 |
| 40 | $CH_3$ | $C_2H_5$ | (3,5-dimethylpyrazolyl) | 0.125 | 90 | — | 100 | — | — | — | 95 | 60 |
| | | | | 0.25 | 100 | 80 | 100 | 30 | 0 | 100 | 98 | 60 |

TABLE 2-continued

Intensity of action of haloacetanilides on certain plants; preemergence treatment in the greenhouse Basic molecule 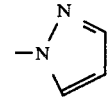

| Compound No. | Substituents R | R¹ | A | Appl. rate kg/ha | Test plants and % damage |||||||
|---|---|---|---|---|---|---|---|---|---|---|---|
| | | | | | Amar. retro. | Bromus spp. | Cyp. diff. | Chrys. seget. | Euph. gen. | Poa annua | Solanum nigrum | Sorgh. halep. |
| 8 | C₂H₅ | C₂H₅ | 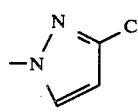 | 0.25 | 95 | 100 | — | — | — | — | — | 85 |
| 70 | C₂H₅ | C₂H₅ | 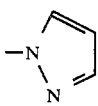 | 0.25 | 100 | 100 | — | — | — | — | — | 75 |

0 = no damage
100 = complete destruction

TABLE 3

Removal of unwanted plants in rape with haloacetanilides; preemergence application in the open Basic molecule 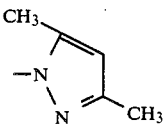

| Compound No. | Substituents R | R¹ | A | Appl. rate kg/ha | Test plants and % damage |||||
|---|---|---|---|---|---|---|---|---|---|
| | | | | | Brassica napus | Alopec. myosur. | Anth./ Matric. | Lamium spp. | Stellaria media |
| 5 | CH₃ | CH₃ | 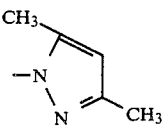 | 2.0 | 7.5 | 95 | 100 | 100 | 100 |
| 40 | CH₃ | C₂H₅ | 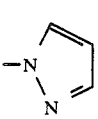 | 1.0 | 20 | 50 | 90 | 60 | 68 |
| 38 | CH₃ | CH₃ | 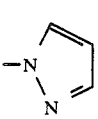 | 2.0 | 0 | 80 | 100 | 100 | 88 |
| 7 | CH₃ | C₂H₅ | 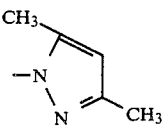 | 0.5 | 5 | 70 | 100 | 95 | 80 |
| | | | | 1.0 | 10 | 85 | — | 100 | 95 |
| 129 | CH₃ | C₂H₅ | 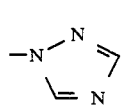 | 2.0 | 7.5 | 35 | 35 | 45 | 24 |
| | | | | 4.0 | 22.5 | 68 | 65 | 90 | 49 |

TABLE 3-continued

Removal of unwanted plants in rape with haloacetanilides; preemergence application in the open Basic molecule: aromatic ring with R (ortho), R$^1$ (ortho), and N(CH$_2$—A)(COCH$_2$Cl)

| Compound No. | Substituents R | R$^1$ | A | Appl. rate kg/ha | Brassica napus | Alopec. myosur. | Anth./ Matric. | Lamium spp. | Stellaria media |
|---|---|---|---|---|---|---|---|---|---|
| 191 | CH$_3$ | C$_2$H$_5$ | —N(pyrazole-N) · HNO$_3$ | 2.0 | 5 | 30 | 53 | 40 | 18 |
|  |  |  |  | 4.0 | 20 | 80 | — | 85 | 45 |
| prior art | C$_2$H$_5$ | C$_2$H$_5$ | —OCH$_3$ | 2.0 | 5 | 65 | 53 | — | 15 |

0 = no damage
100 = no emergence or plants withered

TABLE 4

Herbicidal action of haloacetanilides; postemergence application in the greenhouse Basic molecule: aromatic ring with R (ortho), R$^1$ (ortho), and N(CH$_2$—A)(COCH$_2$Cl)

| Compound No. | Substituents R | R$^1$ | A | Appl. rate kg/ha | Alopec. myosur. | Avena fat. | Cyper. escul. | Chrys. seget. | Matric. spp. | Setaria spp. | Stell. med. |
|---|---|---|---|---|---|---|---|---|---|---|---|
| prior art | C$_2$H$_5$ | C$_2$H$_5$ | —OCH$_3$ | 1.0 | 60 | 50 | 42 | 15 | 50 | 68 | 0 |
|  |  |  |  | 2.0 | 60 | 70 | 55 | 15 | 50 | 68 | 30 |
| 5 | CH$_3$ | CH$_3$ | —N(pyrazole) | 1.0 | 80 | 90 | 70 | 98 | 95 | 82 | 95 |
|  |  |  |  | 2.0 | 90 | 92 | 72 | 98 | 95 | 85 | 98 |
| 38 | CH$_3$ | CH$_3$ | —N(3,5-dimethylpyrazole) | 1.0 | — | 70 | 80 | — | — | 85 | 100 |
|  |  |  |  | 2.0 | — | 90 | 80 | — | — | 85 | 100 |
| 68 | C$_2$H$_5$ | CH$_3$ | —N(3-methylpyrazole) | 1.0 | 90 | 90 | 85 | 40 | 80 | 90 | 60 |
|  |  |  |  | 2.0 | 90 | 90 | 85 | 50 | 80 | 95 | 60 |
| 189 | C$_2$H$_5$ | CH$_3$ | —N(1,2,4-triazole) · HCl | 1.0 | 70 | 60 | 65 | 0 | 30 | 80 | 0 |
|  |  |  |  | 2.0 | 70 | 60 | 65 | 20 | 60 | 85 | 40 |
| 158 | C$_2$H$_5$ | CH$_3$ | —N(3-methyl-1,2,4-triazole) | 1.0 | 70 | 75 | 50 | 20 | 50 | 85 | 0 |
|  |  |  |  | 2.0 | 90 | 75 | 65 | 40 | 95 | 85 | 40 |

0 = no damage
100 = no emergence or plants withered

TABLE 5

Herbicidal action and crop plant tolerance of haloacetanilides; preemergence application in the open Basic molecule: 2,6-disubstituted phenyl with N(CH$_2$—A)(COCH$_2$Cl), R and R$^1$ at the 2 and 6 positions.

| Compound No. | Substituents R | R$^1$ | A | Appl. rate kg/ha | Glyc. max | Amar. retro. | Chenop. spp. | Echin. c.g. | Galins. spp. |
|---|---|---|---|---|---|---|---|---|---|
| 5 | CH$_3$ | CH$_3$ | —N(pyrazol-1-yl) | 0,5 | 0 | 100 | 69 | 100 | 91 |
|   |        |        |                  | 1,0 | 4 | 100 | 85 | 100 | 100 |
| prior art | C$_2$H$_5$ | C$_2$H$_5$ | —OCH$_3$ | 0,1 | 0 | —  | 10 | 65 | 30 |
|   |        |        |          | 1,0 | 0 | 80 | 13 | 73 | 55 |

0 = no damage
100 = no emergence or plants withered

TABLE 6

Tolerance of some haloacetanilides by soybeans and cotton, combined with good herbicidal action; preemergence application in the greenhouse Basic molecule as above.

| Compound No. | Substituents R | R$^1$ | A | Appl. rate kg/ha | Glyc. max | Gossyp. hirs. | Amar. retro. | Cyper. escul. | Echin. c.g. | Euph. genic. | Setaria spp. | Solanum nigrum |
|---|---|---|---|---|---|---|---|---|---|---|---|---|
| prior art | C$_2$H$_5$ | C$_2$H$_5$ | —OCH$_3$ | 0,5 | 0 | 0 | 100 | 40 | 65 | 20 | 60 | 95 |
|   |   |   |   | 1,0 | 0 | 20 | 100 | 50 | 90 | 45 | 90 | 100 |
|   |   |   |   | 2,0 | 0 | 40 | 100 | 60 | 95 | 100 | 100 | 100 |
| 68 | C$_2$H$_5$ | CH$_3$ | —N(3-methylpyrazol-1-yl) | 0,25 | 0 | 0 | 95 | 65 | 95 | 10 | 95 | 95 |
|   |   |   |   | 1,0 | 0 | 5 | 100 | 80 | 95 | 60 | 100 | 100 |
|   |   |   |   | 2,0 | 10 | 5 | 100 | 80 | 95 | 75 | 100 | 100 |
| 189 | C$_2$H$_5$ | CH$_3$ | —N(imidazol-1-yl)·HCl | 0,5 | 0 | 0 | 30 | 50 | 90 | 90 | 75 | 30 |
|   |   |   |   | 1,0 | 0 | 20 | 95 | 60 | 95 | 95 | 95 | 95 |
|   |   |   |   | 2,0 | 0 | 20 | 95 | 80 | 95 | 95 | 100 | 95 |
| 158 | C$_2$H$_5$ | CH$_3$ | —N(2-methylimidazol-1-yl) | 0,5 | 0 | 0 | 95 | 55 | 95 | 60 | 90 | 95 |
|   |   |   |   | 1,0 | 10 | 0 | 100 | 75 | 95 | 90 | 95 | 100 |
|   |   |   |   | 2,0 | 20 | 10 | 100 | 75 | 95 | 90 | 100 | 100 |
| 130 | C$_2$H$_5$ | C$_2$H$_5$ | —N(imidazol-1-yl) | 0,5 | 20 | 20 | 95 | 40 | 95 | 60 | 85 | 100 |
|   |   |   |   | 1,0 | 20 | 30 | 100 | 70 | 100 | 60 | 95 | 100 |
|   |   |   |   | 2,0 | 20 | 30 | 100 | 80 | 100 | 100 | 100 | 100 |
| 159 | C$_2$H$_5$ | C$_2$H$_5$ | —N(2-methylimidazol-1-yl) | 0,5 | 0 | 0 | 85 | 40 | 80 | 20 | 75 | 50 |
|   |   |   |   | 1,0 | 0 | 10 | 95 | 65 | 95 | 50 | 90 | 95 |
|   |   |   |   | 2,0 | 0 | 20 | 100 | 70 | 100 | 55 | 100 | 95 |

0 = no damage
100 = plants withered

TABLE 7

Selective herbicidal action of haloacetanilides; preemergence application in the greenhouse

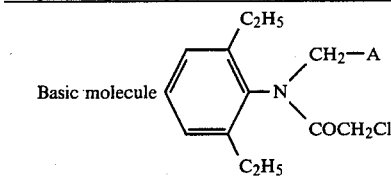

Basic molecule

| Compound No. | Substituent A | Appl. rate kg/ha | Glyc. max | Gossyp. hirs. | Amar. retro. | Cenchr. ech. | Cyp. diff. | Echin. c.g. | Ipom. spp. | Lept. spp. | Panic. virg. | Sida spin. | Solan. nigr. |
|---|---|---|---|---|---|---|---|---|---|---|---|---|---|
| 41 | (pyrazole structure with CH₃, N-N, CH₃) | 0,25 | 0 | 0 | 73 | 90 | 100 | 95 | — | 95 | 85 | — | 70 |
|  |  | 0,5 | 0 | 8 | 97 | 92 | 100 | 100 | — | 95 | 85 | — | 90 |
|  |  | 1,0 | 0 | 8 | 100 | 100 | 100 | 100 | 50 | 95 | 100 | 45 | 98 |
|  |  | 2,0 | 0 | 10 | 100 | 100 | — | 100 | 90 | 95 | 100 | 90 | 100 |
| bekannt | —OCH₃ | 0,25 | 0 | 0 | 68 | 92 | 65 | 45 | — | 100 | 30 | — | 50 |
|  |  | 0,5 | 0 | 6 | 81 | 95 | 70 | 75 | — | 100 | 45 | — | 73 |
|  |  | 1,0 | 0 | 20 | 88 | 100 | 78 | 90 | 20 | 100 | 92 | 10 | 90 |
|  |  | 2,0 | 0 | 45 | 92 | 100 | 100 | 95 | 30 | 100 | 100 | 70 | 90 |

0 = no damage
100 = no emergence or plants withered

TABLE 8

Tolerance of a further herbicidal haloacetanilide by various oil crops in the greenhouse

| Compound no. | Structure | Appl. rate kg/ha | Brassica napus | Glyc.ˣ max | Arach. hypog. | Carth. tinct. | Amar. retro. | Seta. spp. | Solan. nigrum. |
|---|---|---|---|---|---|---|---|---|---|
| 127 | (structure shown) | 0,5 | 0 | 0 | 0 | 0 | 82 | 95 | 70 |
|  |  | 1,0 | 0 | 0 | 0 | 0 | 95 | 100 | 90 |
|  |  | 2,0 | 0 | 0 | 10 | — | 100 | 100 | 100 |

0 = no damage
100 = no emergence or plants withered
ˣvarieties: Dare, Lee 68, SRF 450

TABLE 9

Tolerance and herbicidal action of haloacetanilides in various crops; preemergence application in the greenhouse

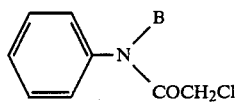

Basic molecule

| Compound No. | Substituent B | Appl. rate kg/ha | Glyc. max | Sorgh. bic. | Zea mays | Amar. retro. | Bromus spp. | Echin. c.g. | Setar. spp. |
|---|---|---|---|---|---|---|---|---|---|
| prior art | C₃H₇i | 1.0 | 10 | 0 | 0 | 42 | 50 | 45 | 95 |
|  |  | 2.0 | 40 | 0 | 0 | 50 | 70 | 90 | 100 |
| 34 | —CH₂—N(pyrazole with CH₃, CH₃) | 1.0 | 0 | 0 | 0 | 100 | 95 | 90 | 80 |
|  |  | 2.0 | 0 | 10 | 0 | 100 | 95 | 90 | 95 |

0 = no damage
100 = no emergence or plants withered

TABLE 10

Herbicidal action of selective haloacetanilides; preemergence application in the greenhouse Basic molecule:

$$\text{R, R}^1\text{, R}^2\text{-substituted phenyl-N(CH}_2\text{-A)(COCH}_2\text{Cl)}$$

| Compound no. | R | R¹ | R² | A | Appl. rate kg/ha | Glyc. max | Gos. syp. hirs. | Alopec. myosur. | Amar. retro. | Cyp. diff. | Echin. c.g. | Euph. gen. | Matric. spp. | Setaria spp. | Sorg. halep. | Stell. med. |
|---|---|---|---|---|---|---|---|---|---|---|---|---|---|---|---|---|
| prior art | CH₃ | CH₃ | H | -CH(O-CH₂)(O-CH₂) | 0.25 | 10 | 0 | 40 | 80 | 100 | 95 | 15 | 50 | 70 | 30 | 20 |
|  |  |  |  |  | 0.5 | 20 | 0 | 80 | 80 | 100 | 100 | 30 | 80 | 90 | 40 | 70 |
|  |  |  |  |  | 1.0 | 25 | 10 | 80 | 100 | 100 | 100 | 50 | 90 | 100 | 70 | 70 |
| 14 | CH₃ | CH₃ | CH₃ | -N(pyrazolyl) | 0.25 | 10 | 0 | 95 | 100 | 100 | 100 | 80 | 80 | 100 | 95 | 90 |
|  |  |  |  |  | 0.5 | 10 | 0 | 100 | 100 | 100 | 100 | 95 | 100 | 100 | 95 | 100 |
|  |  |  |  |  | 1.0 | 20 | 15 | 100 | 100 | 100 | 100 | 95 | 100 | 100 | 100 | 100 |
| 47 | CH₃ | CH₃ | CH₃ | -N(3,5-dimethylpyrazolyl) | 0.25 | 20 | 0 | 95 | 100 | 100 | 95 | 10 | 80 | 100 | 85 | 30 |
|  |  |  |  |  | 0.5 | 20 | 0 | 100 | 100 | 100 | 95 | 10 | 90 | 100 | 90 | 80 |
|  |  |  |  |  | 1.0 | 30 | 0 | 100 | 100 | 100 | 100 | 20 | 100 | 100 | 95 | 100 |
| 136 | CH₃ | CH₃ | CH₃ | -N(1,2,4-triazolyl) | 0.25 | — | — | — | — | — | — | — | — | — | — | — |
|  |  |  |  |  | 0.5 | 0 | 10 | 50 | 70 | 90 | 95 | 45 | 50 | 90 | 80 | 30 |
|  |  |  |  |  | 1.0 | 10 | 10 | 90 | 70 | 90 | 95 | 65 | 90 | 100 | 80 | 80 |

0 = no damage
100 = no emergence or plants withered

TABLE 11

Herbicidal action of further haloacetanilides; preemergence application in the greenhouse Basic molecule:

$$\text{R, R}^1\text{, R}^2\text{, R}^3\text{, R}^4\text{-substituted phenyl-N(CH}_2\text{-A)(COCH}_2\text{Cl)}$$

| Compound No. | R¹ | R² | R³ | R⁴ | R | A | Appl. rate kg/ha | Alopec. myosur. | Amar. retro. | Cyper. diff. | Echin. c.g. | Set. spp. | Sorgh. hale. |
|---|---|---|---|---|---|---|---|---|---|---|---|---|---|
| 162 | C₂H₅ | H | H | H | C₂H₅ | -N(3,5-dimethyl-1,2,4-triazolyl) | 2.0 | 95 | 100 | 100 | 100 | 100 | 95 |
| 4 | H | H | H | H | i-C₃H₇ | -N(pyrazolyl) | 2.0 | 95 | 95 | 90 | 100 | 90 | 65 |
| 17 | CH₃ | CH₃ | H | H | H | -N(pyrazolyl) | 2.0 | 50 | 90 | 100 | 100 | 90 | 75 |
| 9 | i-C₃H₇ | H | H | H | CH₃ | -N(pyrazolyl) | 2.0 | 100 | 100 | 100 | 100 | 100 | 90 |

TABLE 11-continued

Herbicidal action of further haloacetanilides; preemergence application in the greenhouse Basic molecule

[Structure: phenyl ring with R at 2-position, R¹ at 6-position, R² at 5-position, R³ at 4-position, R⁴ at 3-position, and N substituted with CH₂—A and COCH₂Cl]

| Compound No. | Substituents R¹ | R² | R³ | R⁴ | R | A | Appl. rate kg/ha | Alopec. myosur. | Amar. retro. | Cyper. diff. | Echin. c.g. | Set. spp. | Sorgh. hale. |
|---|---|---|---|---|---|---|---|---|---|---|---|---|---|
| 11 | i-C₃H₇ | H | H | H | i-C₃H₇ | —N(pyrazolyl) | 2.0 | 90 | 90 | 100 | 100 | 80 | 70 |
| 13 | CH₃ | H | CH₃ | H | CH₃ | —N(pyrazolyl) | 2.0 | 80 | 100 | 90 | 100 | 90 | 80 |
| 108 | C₂H₅ | H | H | H | C₂H₅ | —N(3,5-dimethyl-4-chloropyrazolyl) | 2.0 | 70 | 100 | 100 | 100 | 90 | 60 |
| 139 | CH₃ | CH₃ | H | H | H | —N(1,2,4-triazolyl) | 2.0 | 70 | 40 | 90 | 90 | 30 | 50 |
| 36 | H | H | H | H | C₂H₅ | —N(3,5-dimethylpyrazolyl) | 0.5 | 90 | 95 | — | 80 | 90 | 40 |
|  |  |  |  |  |  |  | 1.0 | 100 | 95 | — | 95 | 95 | 40 |
| 131 | i-C₃H₇ | H | H | H | CH₃ | —N(1,2,4-triazolyl) | 2.0 | 70 | 80 | 100 | 100 | 100 | 80 |
| 37 | H | H | H | H | i-C₃H₇ | —N(3,5-dimethylpyrazolyl) | 1.0 | 30 | 100 | 100 | 100 | 100 | 80 |
| 50 | CH₃ | CH₃ | H | H | H | —N(3,5-dimethylpyrazolyl) | 1.0 | 90 | 100 | 100 | 100 | 100 | 70 |
| 52 | CH₃ | H | H | CH₃ | H | —N(3,5-dimethylpyrazolyl) | 2.0 | 60 | 100 | 100 | 95 | 90 | 60 |
| 42 | i-C₃H₇ | H | H | H | CH₃ | —N(3,5-dimethylpyrazolyl) | 1.0 | 95 | 100 | 100 | 100 | 100 | 90 |

TABLE 11-continued
Herbicidal action of further haloacetanilides; preemergence application in the greenhouse Basic molecule:

R group structure with R, R², R³, R⁴ substituents on phenyl ring, N-CH₂-A, N-COCH₂Cl

| Compound No. | Substituents R¹ | R² | R³ | R⁴ | R | A | Appl. rate kg/ha | Alopec. myosur. | Amar. retro. | Cyper. diff. | Echin. c.g. | Set. spp. | Sorgh. hale. |
|---|---|---|---|---|---|---|---|---|---|---|---|---|---|
| 44 | i-C₃H₇ | H | H | H | i-C₃H₇ | 3,5-dimethylpyrazol-1-yl | 2.0 | 80 | 80 | 100 | 90 | 90 | 40 |
| 46 | CH₃ | H | CH₃ | H | CH₃ | 3,5-dimethylpyrazol-1-yl | 1.0 | 60 | 90 | 100 | 100 | 100 | 80 |

0 = no damage
100 = no emergence or plants withered

TABLE 12
Herbicidal acetanilides selective in sugarbeet and other crops; preemergence application in the greenhouse Basic molecule: phenyl ring with R, R¹, R² substituents, N-CH₂-A, N-C(=O)-CH₂Cl

| Compound no. | Substituents R | R¹ | R² | A | Appl. rate ka/ha | Beta vulg. | Glyc. max | Sorgh. bicol. | Zea mays | Alopec. myosur. | Amar. retro. | Setaria spp. |
|---|---|---|---|---|---|---|---|---|---|---|---|---|
| 107 | CH₃ | C₂H₅ | H | 4-chloro-3,5-dimethylpyrazol-1-yl | 2.0 | 0 | 0 | 85 | 0 | 95 | 95 | 95 |
| 106 | CH₃ | CH₃ | H | 4-chloro-3,5-dimethylpyrazol-1-yl | 1.0 | 10 | 10 | 70 | 15 | 100 | 95 | 90 |
| | | | | | 2.0 | 10 | 10 | 70 | 50 | 100 | 95 | 95 |
| 72 | i-C₃H₇ | H | H | 3-methylpyrazol-1-yl | 1.0 | 10 | 10 | 20 | 0 | 100 | 95 | 90 |
| | | | | | 2.0 | 10 | 20 | 40 | 10 | 100 | 95 | 95 |
| 69 | C₂H₅ | H | H | 3-methylpyrazol-1-yl | 0.5 | 20 | 20 | 10 | 0 | 100 | 95 | 80 |

TABLE 12-continued

Herbicidal acetanilides selective in sugarbeet and other crops; preemergence application in the greenhouse Basic molecule 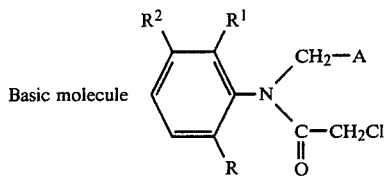

| Compound no. | Substituents | | | | Appl. rate ka/ha | Test plants and % damage | | | | | | |
|---|---|---|---|---|---|---|---|---|---|---|---|---|
| | R | R[1] | R[2] | A | | Beta vulg. | Glyc. max | Sorgh. bicol. | Zea mays | Alopec. myosur. | Amar. retro. | Setaria spp. |
| 24 | CH$_3$ | H | Cl | -N(pyrazolyl) | 2.0 | 60 | 10 | 10 | 0 | 100 | 95 | 85 |

0 = no damage
100 = no emergence or plants withered

TABLE 13

Basic molecule 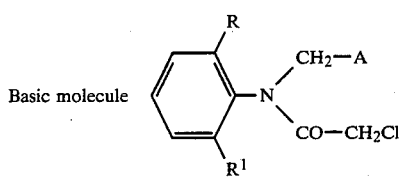

| Substituents | | | Appl. rate | Test plants and % damage | | | |
|---|---|---|---|---|---|---|---|
| R | R[1] | A | ka/ha | Beta vulg. | Alopec. myosur. | Echin c.g. | Setar. spp. |
| CH$_3$ | CH$_3$ | -N(pyrazolyl) | 1.0 | 0 | 20 | 40 | 20 |
| CH$_3$ | CH$_3$ | -N(dichloropyrazolyl) | 0.5 | 0 | 80 | 100 | 100 |
| | | | 1.0 | 0 | 80 | 100 | 100 |
| CH$_3$ | C$_2$H$_5$ | -N(dichloropyrazolyl) | 0.5 | 0 | 100 | 100 | 100 |
| | | | 1.0 | 0 | 100 | 100 | 100 |

0 = no damage
100 = no emergence or plants withered

TABLE 14

Tolerance by various crop plants; preemergence application in the greenhouse

Basic molecule: 2,6-disubstituted-N-(CH₂-A)-N-(COCH₂Cl)aniline (R and R¹ at ortho positions)

| Substituents | | | Appl. rate | Test plants and % damage | | | | | | | |
|---|---|---|---|---|---|---|---|---|---|---|---|
| R | R¹ | A | kg/ha | Beta vulg. | Glyc. max | Alopec. myosur. | Bromus spp. | Cyperus ferax | Echin. c.g. | Matric. spp. | Setaria spp. |
| CH₃ | CH₃ | -N(pyrazol-1-yl)-4-OCH₃ | 0.5 | — | 0 | 100 | 100 | 100 | 100 | 95 | 100 |
| | | | 1.0 | — | 0 | 100 | 100 | 100 | 100 | 95 | 100 |
| CH₃ | C₂H₅ | -N(pyrazol-1-yl)-4-OCH₃ | 0.5 | 5 | 0 | 100 | 90 | 100 | 100 | 98 | 100 |
| | | | 1.0 | 15 | 0 | 100 | 98 | 100 | 100 | 98 | 100 |
| C₂H₅ | C₂H₅ | -N(pyrazol-1-yl)-4-OCH₃ | 1.0 | 10 | 0 | 99 | 98 | 100 | 100 | 90 | 100 |
| | | | 2.0 | 15 | 0 | 99 | 98 | 100 | 100 | 98 | 100 |
| CH₃ | CH₃ | -N(pyrazol-1-yl)-4-CH₃ | 0.5 | 0 | 0 | 90 | 95 | — | 98 | 100 | 92 |
| | | | 1.0 | 0 | 10 | 95 | 95 | — | 98 | 100 | 100 |
| CH₃ | CH₃ | -N(pyrazol-1-yl)-4-Cl | 1.0 | 3 | 5 | 95 | 92 | — | 100 | 75 | 95 |
| | | | 2.0 | 13 | 20 | 100 | 95 | — | 100 | 80 | 100 |
| CH₃ | C₂H₅ | -N(pyrazol-1-yl)-4-Cl | 1.0 | 0 | — | 90 | 90 | — | 100 | 60 | 85 |
| CH₃ | C₂H₅ | -N(pyrazol-1-yl)-4-CH₃ | 3.0 | — | — | — | — | — | 100 | — | — |

0 = no damage

100 = no emergence or plants withered

TABLE 15

Preemergence application in the greenhouse

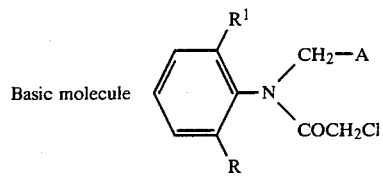

Basic molecule

| Substituents | | | | Test plants and % damage | | | | | | | | | |
|---|---|---|---|---|---|---|---|---|---|---|---|---|---|
| R | R¹ | A | kg/ha | Arach. hypog. | Brassica napus | Zea mays | Alopec. myosur. | Bromus spp. | Cyp. diff. | Echin. c.g. | Matric. spp. | Setar. spp. | Solan. nigr. |
| CH₃ | CH₃ | -N-pyrazole(OCH₃, CH₃) | 0.5 | 0 | 5 | 20 | 95 | 95 | 100 | 90 | 95 | 98 | 85 |
| H | CH₃ | -N-pyrazole(CH₃, CH₃) | 1.0 | — | 10 | 0 | 85 | 95 | — | 85 | 90 | 60 | 100 |
| H | CH₃ | -N-pyrazole | 2.0 | — | 0 | 15 | 90 | 80 | — | 95 | 90 | 95 | 95 |
| H | CH₃ | -N-pyrazole(CH₃) | 2.0 | — | 10 | 0 | 90 | 90 | — | 95 | 90 | 100 | 100 |
| H | CH₃ | -N-pyrazole(CH₃,CH₃,CH₃) | 2.0 | — | 30 | 10 | 50 | 80 | — | 55 | 95 | 100 | 100 |
| CH₃ | CH₃ | -N-triazole(CH₃) | 1.0 | 0 | 5 | — | 97 | 98 | 100 | 100 | 92 | 100 | 100 |
| CH₃ | CH₃ | -N-tetrazole | 2.0 | 15 | — | 15 | 98 | 98 | — | 100 | 100 | 95 | — |

We claim:

1. An acetanilide of the formula

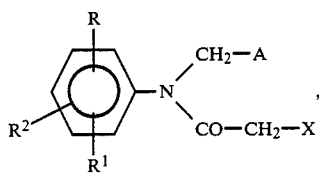

I where R is hydrogen, alkyl of a maximum of 5 carbon atoms, or alkoxy of a maximum of 5 carbon atoms, R' is hydrogen, halogen, alkyl of a maximum of 5 carbon atoms, alkoxy of a maximum of 5 carbon atoms, perhaloalkyl of a maximum of 4 carbon atoms, or alkoxyalkyl of a maximum of 5 carbon atoms, R² is hydrogen, halogen, alkyl of a maximum of 5 carbon atoms, alkoxy of a maximum of 5 carbon atoms, perhaloalkyl of a maximum of 4 carbon atoms, or alkoxyalkyl of a maximum of 5 carbon atoms, X is chloro, bromo, or iodo, and A is azole selected from the group consisting of 1,2,4-triazole and 1,2,3-triazole which is linked via a ring nitrogen atom and is unsubstituted or mono- or polysubstituted by halogen, phenyl, alkyl, alkoxy, alkylthio or perfluoroalkyl, each of maximum of 4 carbon atoms, or A is an acid addition salt of the azole cyano, carboxy, carbalkoxy of a maximum of 4 carbon atoms in the alkoxy group, or alkanoyl of a maximum of 4 carbon atoms.

2. An acetanilide of the formula

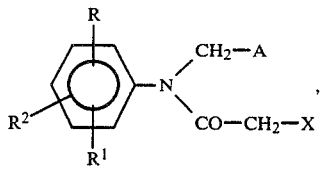

I where R is hydrogen, alkyl of a maximum of 5 carbon atoms, or alkoxy of a maximum of 5 carbon atoms, R' is hydrogen, halogen, alkyl of a maximum of 5 carbon atoms, alkoxy of a maximum of 5 carbon atoms, perhaloalkyl of a maximum of 4 carbon atoms, or alkoxyalkyl of a maximum of 5 carbon atoms, $R^2$ is hydrogen, halogen, alkyl of a maximum of 5 carbon atoms, alkoxy of a maximum of 5 carbon atoms, perhaloalkyl of a maximum of 4 carbon atoms, or alkoxyalkyl of a maximum of 5 carbon atoms, X is chloro, bromo, or iodo, and A is a $C_1$–$C_4$ alkoxy substituted pyrazole which is linked via a ring nitrogen atom, or A is an acid addition salt of the $C_1$–$C_4$ alkoxy substituted pyrazole.

3. An acetanilide of the formula I as defined in claim 1, wherein A is a 1,2,3-triazole group.

4. An acetanilide of the formula I as defined in claim 1, wherein A is a 1,2,4-triazole group.

5. An acetanilide as defined in claim 2, wherein the alkoxy is methoxy.

6. An acetanilide as defined in claim 5, wherein X is chloro.

7. 2-Chloro-2',3',6'-trimethyl-N-(pyrazol-1-yl-methyl)acetanilide.

8. 2-chloro-2',6'-dimethyl-N-(3,5-dimethylpyrazol-1-yl-methyl)acetanilide.

9. 2-chloro-2'-6'-dimethyl-N-(1,2,4-triazol-1-yl-methyl)-acetanilide.

10. 2-chloro-2',3',6'-trimethyl-N-(1,2,4-triazol-1-yl-methyl)-acetanilide.

11. 2-chloro-2',6'-diethyl-N-(1,2,4-triazol-1-yl-methyl)-acetanilide.

12. 2-chloro-2',6'-dimethyl-N-(3(5)-methyl-1,2,4-triazol-1-yl-methyl)-acetanilide.

* * * * *